United States Patent [19]
Frye et al.

[11] Patent Number: 6,116,242
[45] Date of Patent: Sep. 12, 2000

[54] OXYGEN-CONSERVING REGULATOR ASSEMBLY

[75] Inventors: Mark R. Frye, Bloomington; John R. Grenaway, Indianapolis; Richard A. Davis, Lafayette; Douglas R. Leithauser, Carmel, all of Ind.

[73] Assignee: Nellcor Puritan Bennett Incorporated, Pleasanton, Calif.

[21] Appl. No.: 08/849,417

[22] PCT Filed: Sep. 27, 1996

[86] PCT No.: PCT/US96/15549

§ 371 Date: Apr. 28, 1997

§ 102(e) Date: Apr. 28, 1997

[87] PCT Pub. No.: WO97/11734

PCT Pub. Date: Apr. 3, 1997

Related U.S. Application Data

[60] Provisional application No. 60/004,463, Sep. 28, 1995.

[51] Int. Cl.$^7$ ........................................... A62B 9/02
[52] U.S. Cl. .................... 128/205.24; 128/205.18
[58] Field of Search .................. 128/205.24, 204.18, 128/204.23, 207.12, 204.26, 204.28

[56] References Cited

U.S. PATENT DOCUMENTS

| | | | |
|---|---|---|---|
| 4,827,964 | 5/1989 | Guido et al. | 137/81.1 |
| 5,360,000 | 11/1994 | Carter | 128/204.26 |
| 5,743,257 | 4/1998 | Koehler et al. | 128/205.24 |
| 5,755,224 | 5/1998 | Good et al. | 128/205.24 |

OTHER PUBLICATIONS

Puritan–Bennett *Oxygen Therapy Regulators* Product Literature, Sep. 1990 (eight pages).
Puritan–Bennett *Companion® 550* Product Literature, Jan. 1992 (two pages).

*Primary Examiner*—John G. Weiss
*Assistant Examiner*—Charles W. Anderson
*Attorney, Agent, or Firm*—Barnes &Thornburg

[57] ABSTRACT

An apparatus is provided for controlling discharge of oxygen from an oxygen supply source to a patient. The apparatus includes an oxygen supply inlet, a pressure regulator coupled to the oxygen supply inlet and configured to reduce pressure of oxygen received from the oxygen supply inlet to a selected magnitude, a flow controller coupled to the pressure regulator and configured to meter oxygen received from the pressure regulator at a selected flow rate, and an oxygen distribution assembly including a pneumatic demand oxygen valve and a conduit conducting oxygen discharged from the flow controller through the pressure regulator to the pneumatic demand oxygen valve for delivery to a patient. The flow controller includes a chamber and a rotary valve for splitting oxygen discharged from the chamber into a first stream in an oxygen supply passageway for use by a patient and a second stream in a diaphragm supply passageway for controlling operation of pneumatic demand oxygen valve.

65 Claims, 13 Drawing Sheets

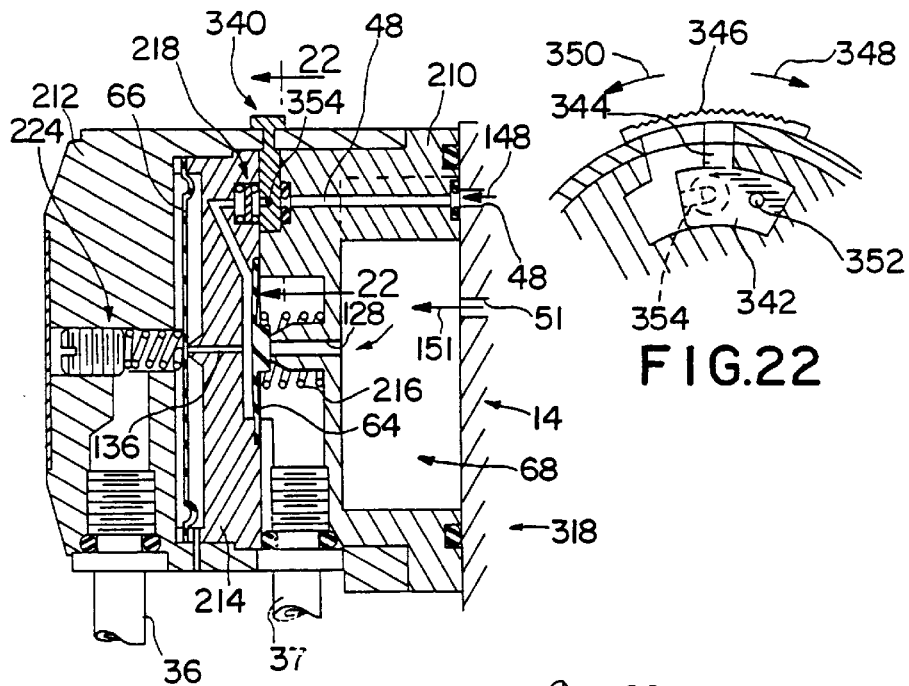
FIG. 21
FIG. 22
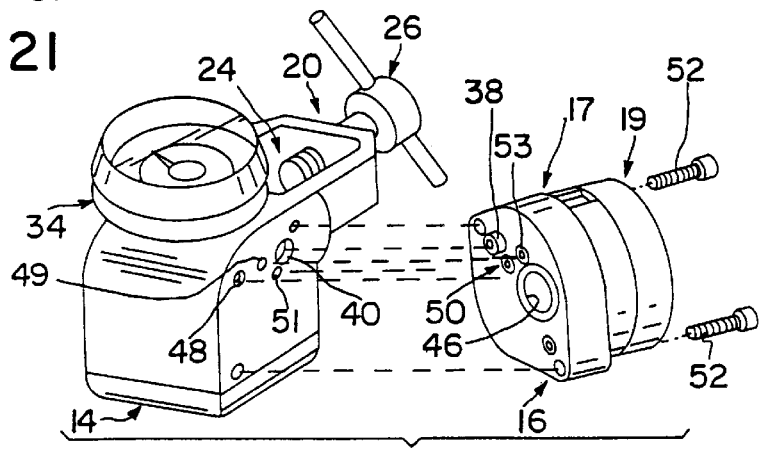
FIG. 23
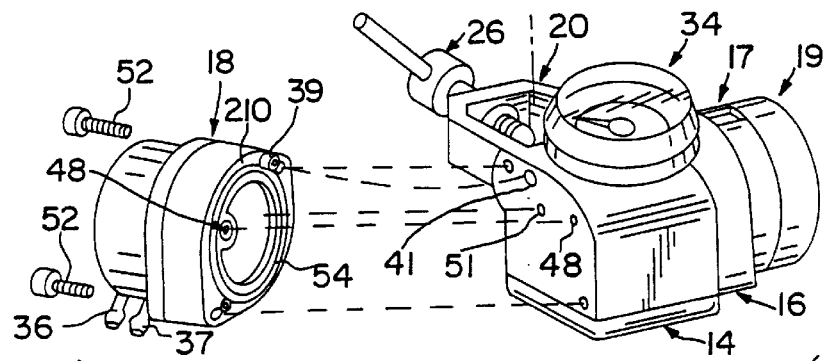
FIG. 24

OXYGEN-CONSERVING REGULATOR ASSEMBLY

CROSS REFERENCES TO RELATED APPLICATIONS

This application is a U.S. national phase counterpart of international application Ser. No. PCT/US96/15549 filed Sep. 27, 1996 which claims priority to United States provisional application Ser. No. 60/004,463 filed Sep. 28, 1995.

BACKGROUND AND SUMMARY OF THE INVENTION

The present invention relates to an oxygen-conserving regulator assembly, and particularly to an oxygen-conserving regulator assembly for use with a high-pressure oxygen system. More particularly, the present invention relates to a modular oxygen-conserving regulator assembly and to an integrated pressure regulator, oxygen-flow control valve, and pneumatic demand oxygen valve assembly.

Supplemental oxygen-delivery systems are provided to administer medicinal gas, normally oxygen, to a patient undergoing respiratory therapy. Supplemental oxygen-delivery systems are used by patients that benefit from receiving and breathing oxygen from an oxygen supply source to supplement atmospheric oxygen breathed by the patients. A compact, portable supplemental oxygen-delivery system is useful in a wide variety of contexts, including hospital, home care, and ambulatory settings.

High-pressure supplemental oxygen-delivery systems typically include a cylinder or tank containing oxygen gas at a pressure of up to 3000 psig. A pressure regulator is used in a high-pressure oxygen-delivery system to "step down" the pressure of oxygen gas in the tank to a lower pressure level (e.g., 20 or 50 psig) suitable for use in an oxygen-delivery apparatus used by a patient in respiratory therapy.

The COMPANION® high-pressure portable oxygen systems available from Nellcor Puritan Bennett Incorporated, Cryogenic Equipment Division, Indianapolis, Ind., USA, include a COMPANIONS 360® regulator/flow controller unit Model No. 77231. This regulator/flow controller unit can be coupled to a high-pressure oxygen gas tank. This regulator/flow controller unit does not include a pneumatic demand valve.

A breathing assist apparatus including a flow controller and a pneumatic demand valve is disclosed in U.S. Pat. No. 5,360,000 to Carter. A flow controller is included in the breathing assist apparatus to meter the flow rate of low-pressure oxygen (typically in liters per minute) delivered to the patient. A pneumatic demand valve is included in the breathing assist apparatus to distribute oxygen to a patient only when oxygen is "demanded" by the patient during inhalation and thus functions to "conserve" oxygen by not distributing oxygen to an exhaling patient. A demand valve delivers a pulse of oxygen at the onset of patient inspiration and continues to deliver oxygen throughout the entire patient inspiration. These demand valves do not deliver oxygen to the patient as the patient exhales.

Pneumatic demand oxygen valves are available from Nellcor Puritan Bennett Incorporated. For example, the COMPANION® 550 is a small lightweight portable liquid oxygen unit with a built-in demand valve and flow controller. A liquid oxygen unit contains liquid oxygen in a reservoir and is very different from a high-pressure oxygen gas cylinder or tank oxygen-delivery system.

What is needed is an oxygen-conserving regulator assembly that is modular and includes a pressure regulator, an oxygen-flow controller, and a pneumatic demand oxygen valve. Consumers would welcome a modular unit that could be reconfigured easily by replacing one modular component such as, for example, the flow controller or the pneumatic demand oxygen valve with another modular component to adapt the modular unit to current needs of a patient.

What is further needed is an integrated pneumatic demand oxygen valve and regulator assembly that is suitable for use with a high-pressure oxygen gas system. Integration of a pneumatic demand oxygen valve in a high-pressure oxygen-delivery system including a pressure regulator, and perhaps also an oxygen-flow controller, would provide a patient using a high-pressure oxygen gas system with the benefits of a pneumatic demand oxygen valve.

What is also needed is an oxygen-flow controller that is operable to provide oxygen to a patient either continuously or on patient demand without requiring a patient to operate a separate continuous/demand oxygen flow selector switch mounted on a separate demand-type pneumatic oxygen valve in the conventional way. Patients would appreciate the ease of using a continuous/demand selector switch integrated in an oxygen-flow controller.

According to the present invention, an apparatus is provided for controlling discharge of oxygen from an oxygen supply source to a patient. The apparatus includes an pressure regulator module, a flow controller module coupled to one side of pressure regulator module, and a pneumatic demand valve module coupled to another side of pressure regulator module. Oxygen is constrained to flow from the oxygen supply along a path to a patient through, in sequence, pressure regulator module, flow controller module, and pneumatic demand valve module.

In preferred embodiments, flow controller module includes an internal chamber for receiving oxygen discharged by the pressure regulator module and a flow control valve positioned to split the flow of oxygen discharged from the internal chamber into a first oxygen stream and a second oxygen stream. The first oxygen stream is conducted along a patient supply conduit through the pressure regulator module and the pneumatic demand valve module to reach a breathing cannula worn by a patient. The second oxygen stream is conducted along an auxiliary conduit through the pressure regulator module to reach and control a valve positioned in the pneumatic demand valve module and pneumatically coupled to an inhale/exhale sensing diaphragm also positioned in the pneumatic demand valve. The flow control valve is a rotary valve that extends into the internal chamber and can be rotated about an axis to adjust flow controller module to operate in either "demand" mode, "continuous" mode, or "off" mode. The flow control valve is movable between a first position range discharging oxygen from the internal chamber into both of the patient supply and auxiliary conduits, a second position range discharging oxygen from the internal chamber into only the patient supply conduit, and a third position range blocking flow of oxygen from the internal chamber into the patient supply and auxiliary conduits.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 21 is a view similar to FIG. 19 of an alternative embodiment of a pneumatic demand valve module configured to include a separate "continuous/demand" flow selector switch in the pneumatic demand valve module;

FIG. 22 is a sectional view of the selector switch taken along line 22—22 of FIG. 21;

FIG. 23 is a perspective view showing assembly of the oxygen-flow controller module onto a right-side face of the pressure regulator module using a mounting orientation post appended to the oxygen-flow controller module;

FIG. 24 is a perspective view showing assembly of the pneumatic demand valve module onto a left-side face of the pressure regulator module using a mounting orientation post appended to the pneumatic demand valve;

DETAILED DESCRIPTION OF THE DRAWINGS

Figure 1:
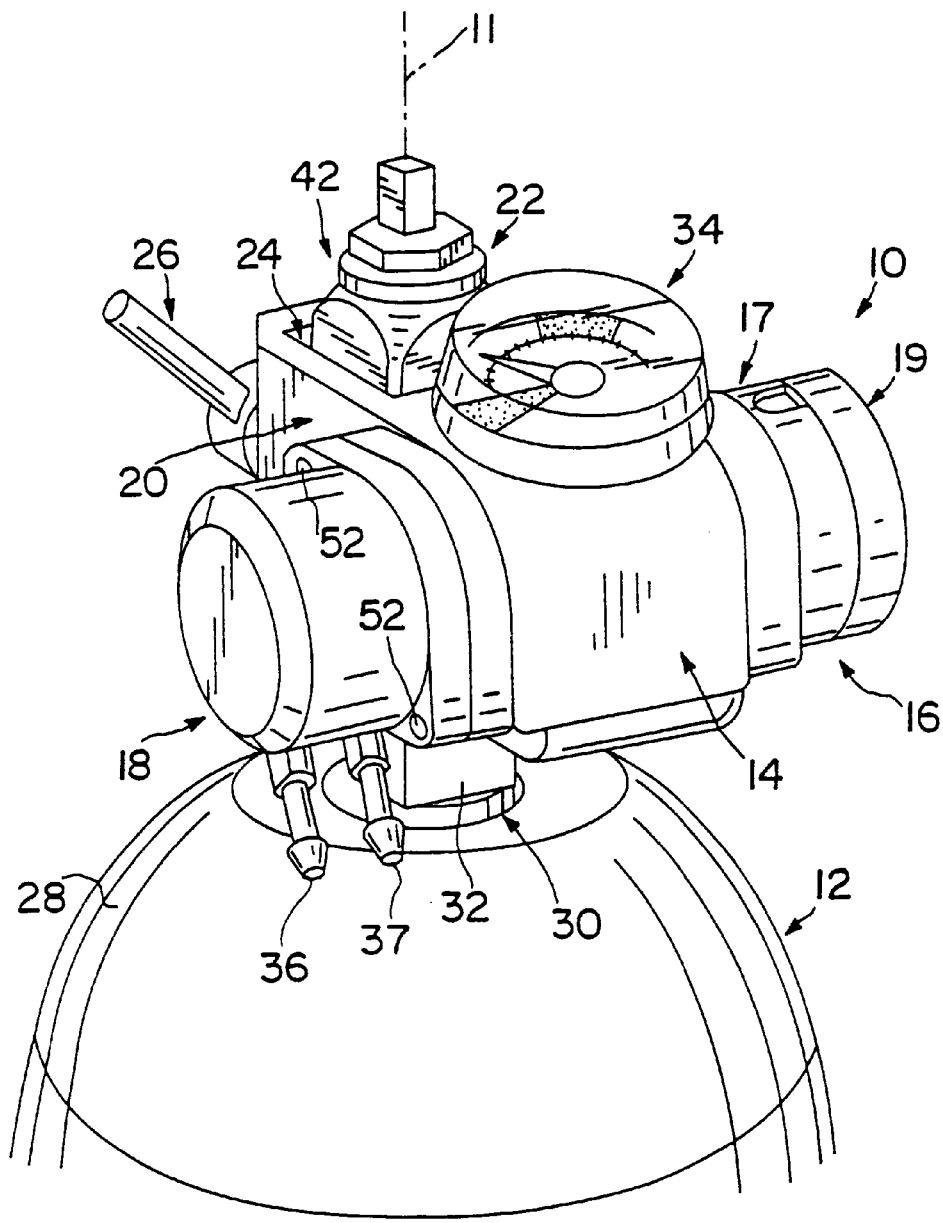
FIG. 1 is a perspective view of a modular oxygen-conserving regulator assembly in accordance with the present invention mounted on an oxygen tank.

An oxygen-conserving regulator assembly 10 is mounted on a cylinder 12 containing oxygen as shown in FIG. 1.

Oxygen-conserving regulator assembly 10 functions as a patient breathing assist apparatus to distribute pressurized oxygen received from cylinder 12 to a patient in need of oxygen at a pressure, flow rate, timing, and mode of delivery (e.g., on-demand flow or continuous flow). Pressure regulator module 14 functions to convert high-pressure oxygen discharged from cylinder 12 into low-pressure oxygen suitable for use in an oxygen-delivery apparatus used by a patient undergoing oxygen therapy. Oxygen-flow controller module 16 functions to meter low-pressure oxygen discharged from pressure regulator module 14 at a certain flow rate (typically measured in liters per minute). Pneumatic demand oxygen valve module 18 functions to take low-pressure, metered oxygen from the oxygen-flow controller module 16 and distribute it to a patient at various times in response to inhalation of the patient through a cannula (see FIGS. 7–9) coupled to pneumatic demand oxygen valve module 18 and worn by the patient.

Oxygen-conserving regulator assembly 10 also includes a yoke 20 connected to regulator module 14 and configured to be connected to post valve 22 as shown, for example, in FIG. 1. Yoke 20 is formed to include a post-receiving channel 24 and T-handle retainer assembly 26 for selectively engaging and fixturing a post valve 22 extending upwardly from cylinder 12 into the post-receiving channel 24 formed in yoke 20.

Cylinder 12 is any cylinder or tank suited for containing high-pressure oxygen. Cylinder 12 includes an upper dome 28 having an oxygen-discharge outlet 30 configured to be coupled in a conventional manner to a lower end 32 of post valve 22 as shown best in FIGS. 2 and 4.

Pressure regulator module 14 carries a pressure gauge 34 for advising a consumer of the remaining oxygen pressure in the cylinder 12. Regulator module 14 is a modular unit that provides reduced-pressure oxygen to flow controller module 16. One reason for mounting the regulator module 14 between flow controller module 16 and demand module 18 is to balance the weight and mass of oxygen-conserving regulator assembly 10 relative to underlying cylinder 12. Regulator module 14 is positioned to lie within the "envelope" of cylinder 12 as shown in FIGS. 1 and 3–5 to keep the center of gravity of assembly 10 as close as possible to the vertical central axis 11 through cylinder 12.

One reason for routing the oxygen gas back and forth across the regulator module 14 as disclosed herein is to permit a design that keeps the mass of regulator assembly 10 near the vertical central axis 11 of cylinder 12. This helps with stability and packaging concerns. Conventional regulator/flow-control devices tend to be linear and extend out a distance from the central vertical axis of a cylinder like cylinder 12.

The flow controller module 16 shown in the drawings is a variable flow meter configured so that a user can select the flow rate of oxygen to be discharged into the pneumatic demand module 18 for delivery to a patient. Flow controller module 16 is a modular unit including a base 17 and a flow selector knob 19 movable relative to base 17 to change the flow rate of oxygen discharged from flow controller module 16.

It is within the scope of this invention to use a flow controller that contains a preset fixed orifice flow meter instead of a variable flow meter as shown in the drawings. The type of flow controller module 16 is not limited to a fixed orifice. It would be possible to use a Thorp tube type of controller (similar to a needle valve which includes a floating ball indicator).

Figure 7:
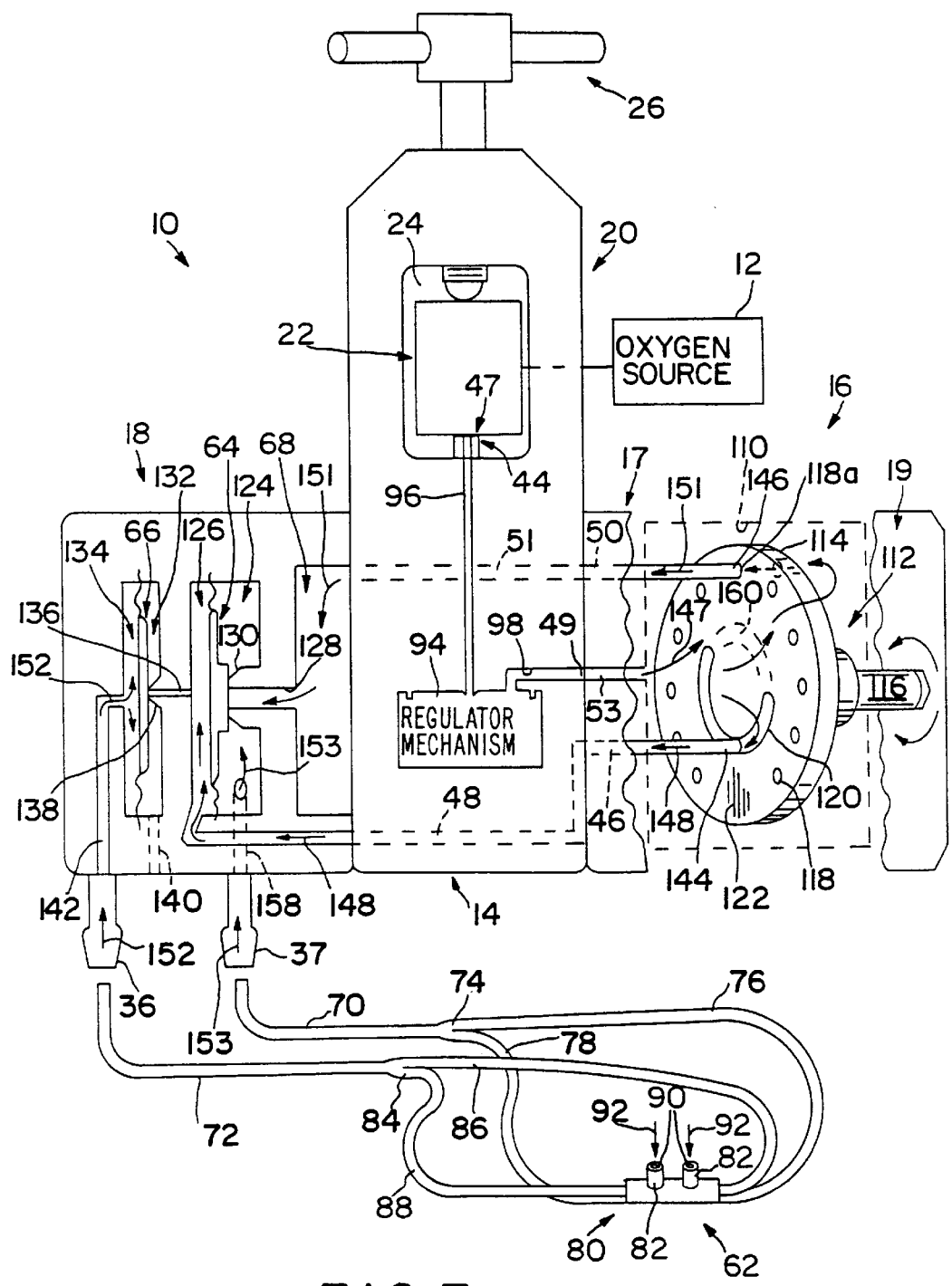
FIG. 7 is a schematic view of the assembly of FIG. 1 coupled to a patient breathing cannula showing a rotary valve in the right-side oxygen-flow controller module positioned in a "demand" mode (i.e., first position range) to distribute a portion of the oxygen received from the regulator module through a diaphragm supply passageway formed in the regulator module to a diaphragm biasing chamber formed in the left-side pneumatic demand valve module and to distribute another portion of the oxygen through a patient supply passageway formed in the regulator module to an oxygen supply chamber formed in the pneumatic demand valve module and showing that the oxygen pressure in the diaphragm biasing chamber is high enough to move a diaphragm valve member to a closed position blocking discharge of oxygen from the oxygen supply chamber to an exhaling patient wearing the patient breathing cannula.

Oxygen that is discharged from flow controller module 16 passes through at least one oxygen-delivery channel (two channels 48, 51 are shown in FIG. 7) formed in regulator module 14 to reach demand module 18. Flow controller module 16 is configured in accordance with the present invention so that it can be operated by a patient to split the incoming flow of low-pressure oxygen received from the regulator module 14 in the flow controller module 16 into two oxygen flow streams 151, 148. In the manner explained in more detail below, one of the oxygen flow streams 151 will be used to supply oxygen via demand module 18 to the patient using regulator assembly 10 and the other oxygen flow stream 148 will be used to control opening and closing of a diaphragm valve member (see FIGS. 7, 7A, 19, and 20) included in demand module 18 to regulate supply of oxygen to the patient using regulator assembly 10.

Demand module 18 includes a suitable pneumatic demand valve system of the type designed for coupling between a source of pressurized gas and a recipient user. This pneumatic demand valve achieves a high degree of sensitivity and flow control without expensive, bulky valving arrangements characteristic of many demand valves.

Demand module 18 includes a sensing port 36 and a gas outlet 37. A cannula 62 (shown in FIGS. 7–9) is coupled to port 36 and gas outlet 37 to enable a patient to receive oxygen from and communicate breath inputs (e.g., inhalation suction and exhalation pressure) to demand module 18.

Figure 2:
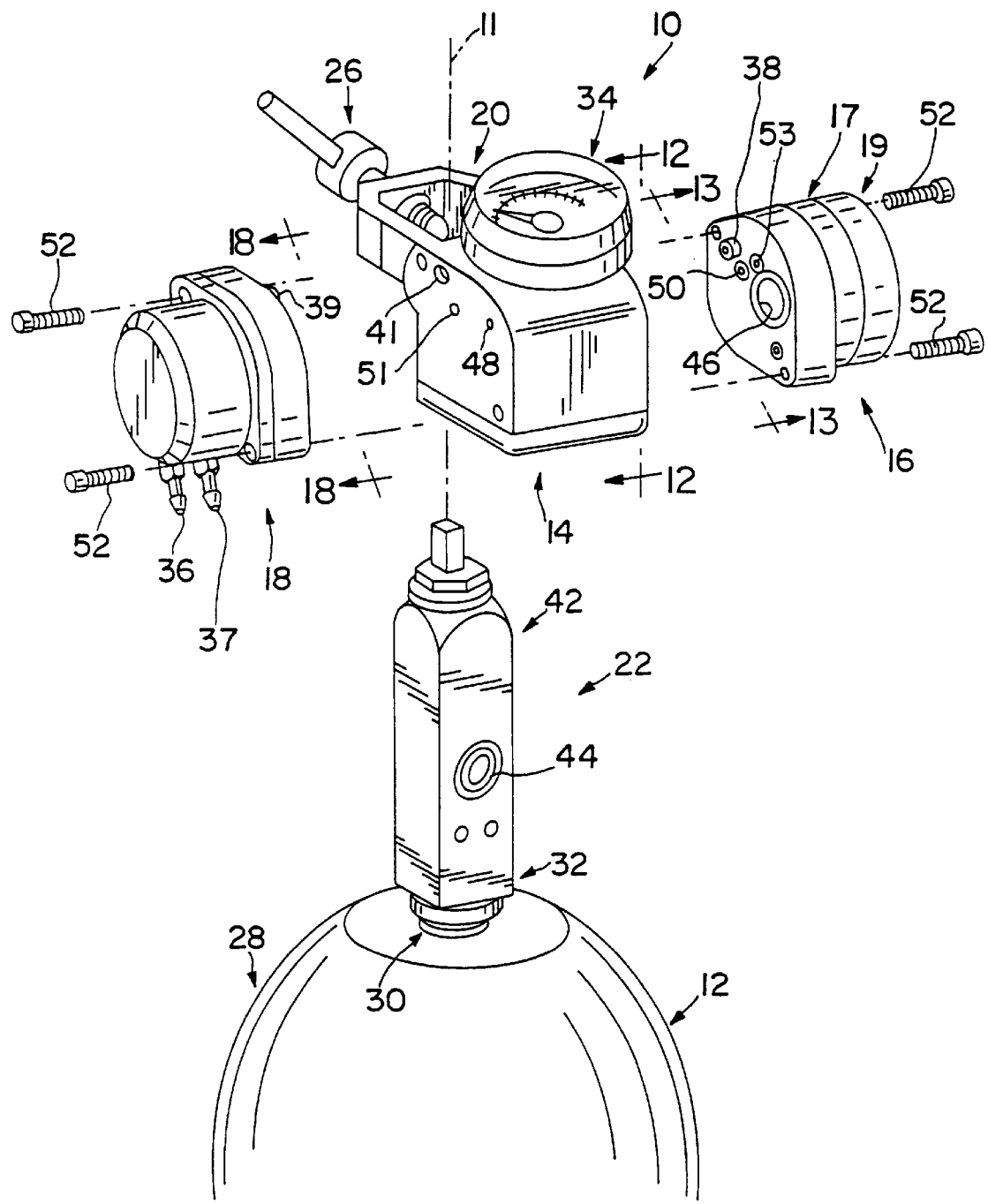
FIG. 2 is an exploded view of the modular regulator assembly of FIG. 1 showing a central pressure regulator module for mounting on the underlying oxygen tank, a right-side oxygen-flow controller module, and a left-side pneumatic demand oxygen valve module for delivering oxygen to a patient through one tube and receiving a signal that the patient is inhaling or exhaling through another tube.

The modular nature of oxygen-conserving regulator assembly 10 is shown, for example, in FIG. 2. In this exploded assembly view, one can see an upright post valve 22 coupled to oxygen-discharge outlet 30 on oxygen cylinder 12. Pressure regulator module 14 is integrally coupled to yoke 20 and arranged so that an upper end 42 of post valve 22 can pass through post-receiving channel 24 formed in yoke 20. Post valve 22 includes an oxygen-discharge outlet 44 for discharging high-pressure oxygen from cylinder 12 into an inlet orifice 47 (shown in FIG. 7) formed in pressure regulator 14. An example of a suitable post valve 22 is a CGA (Compressed Gas Association) 870 yoke valve.

Figure 13:
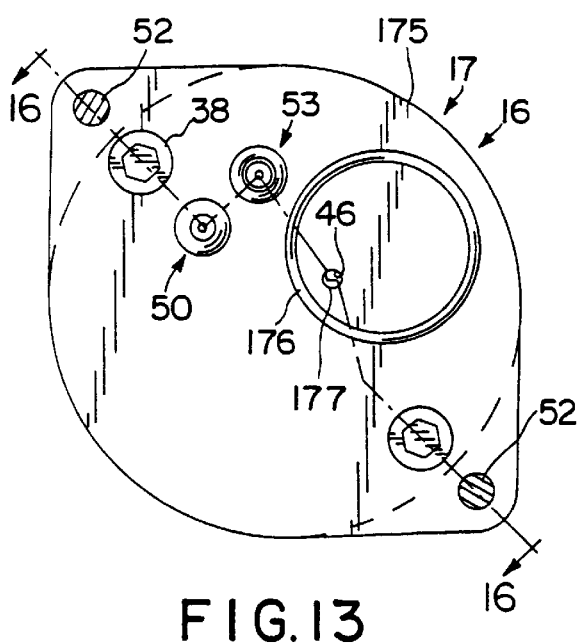
FIG. 13 is an elevational view of the left side of the oxygen-flow controller module taken from line 13—13 of FIG. 2 looking toward the oxygen-flow controller module.

In the illustrated embodiment, bolts 52 and O-ring sealing gasket 54 are used to establish sealed, mounting connections between the pressure regulator module 14 and pneumatic demand oxygen valve module 18. Bolts 52 and a variety of O-ring seals are also used as shown in FIG. 13 to establish sealed mounting connections between flow controller module 16 and pressure regulator module 14. It is within the scope of the present invention to use a variety of suitable detachable connector means for attaching regulator module 14 to each of flow controller module 16 and demand module 18. For example, a threaded connection system, a bayonet connection system, or a ball and race attachment connection system could be used to couple these modular components to one another.

Figure 3:
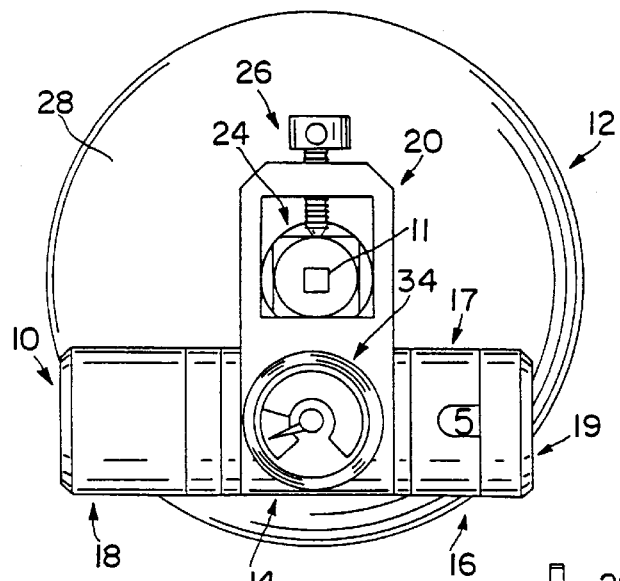
FIG. 3 is a top plan view of the regulator assembly and tank shown in FIG. 1.

Turning now to FIG. 3, which is a plan view of oxygen-conserving regulator assembly 10 and cylinder 12, it will be seen that the T-handle retainer assembly is rotatably mounted on one end of yoke 20 and operable to engage and couple post valve 22 to regulator module 14. A suitable T-handle retainer assembly is disclosed in U.S. Pat. No. 4,752,089. In the illustrated embodiment, regulator module 14 is positioned to lie between demand module 18 and flow controller module 16. In an alternative embodiment (not shown), flow controller valve module 16 could be positioned to lie between regulator module 14 and demand module 18.

Figure 4:
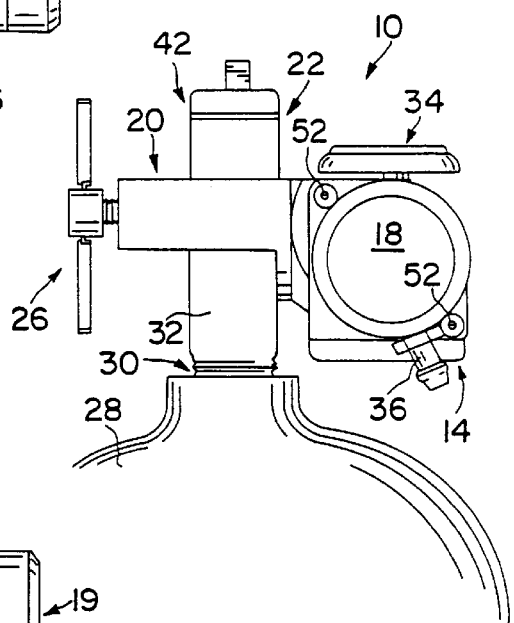
FIG. 4 is a left-side elevational view of the regulator assembly and tank shown in FIG. 1.
Figure 5:
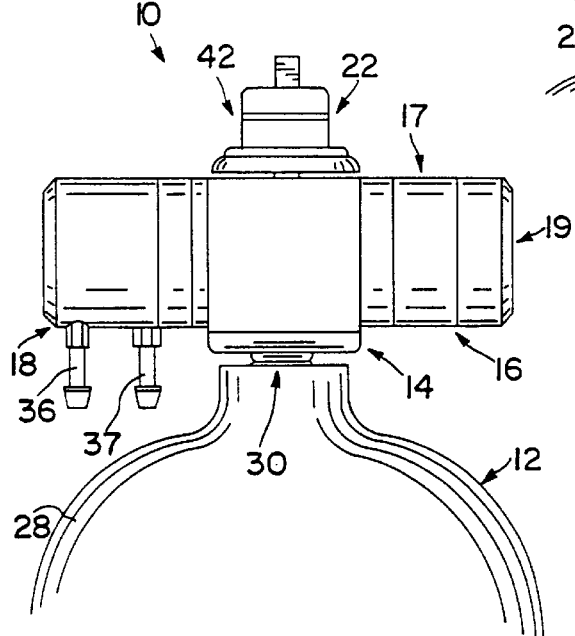
FIG. 5 is a front elevational view of the regulator assembly and tank shown in FIG. 1.

A side elevation of oxygen-conserving regulator assembly 10 in a mounted position on top of oxygen cylinder 12 is shown in FIG. 4. Also, a front elevation view of oxygen-conserving regulator assembly 10 mounted on cylinder 12 is shown in FIG. 5.

Figure 6:
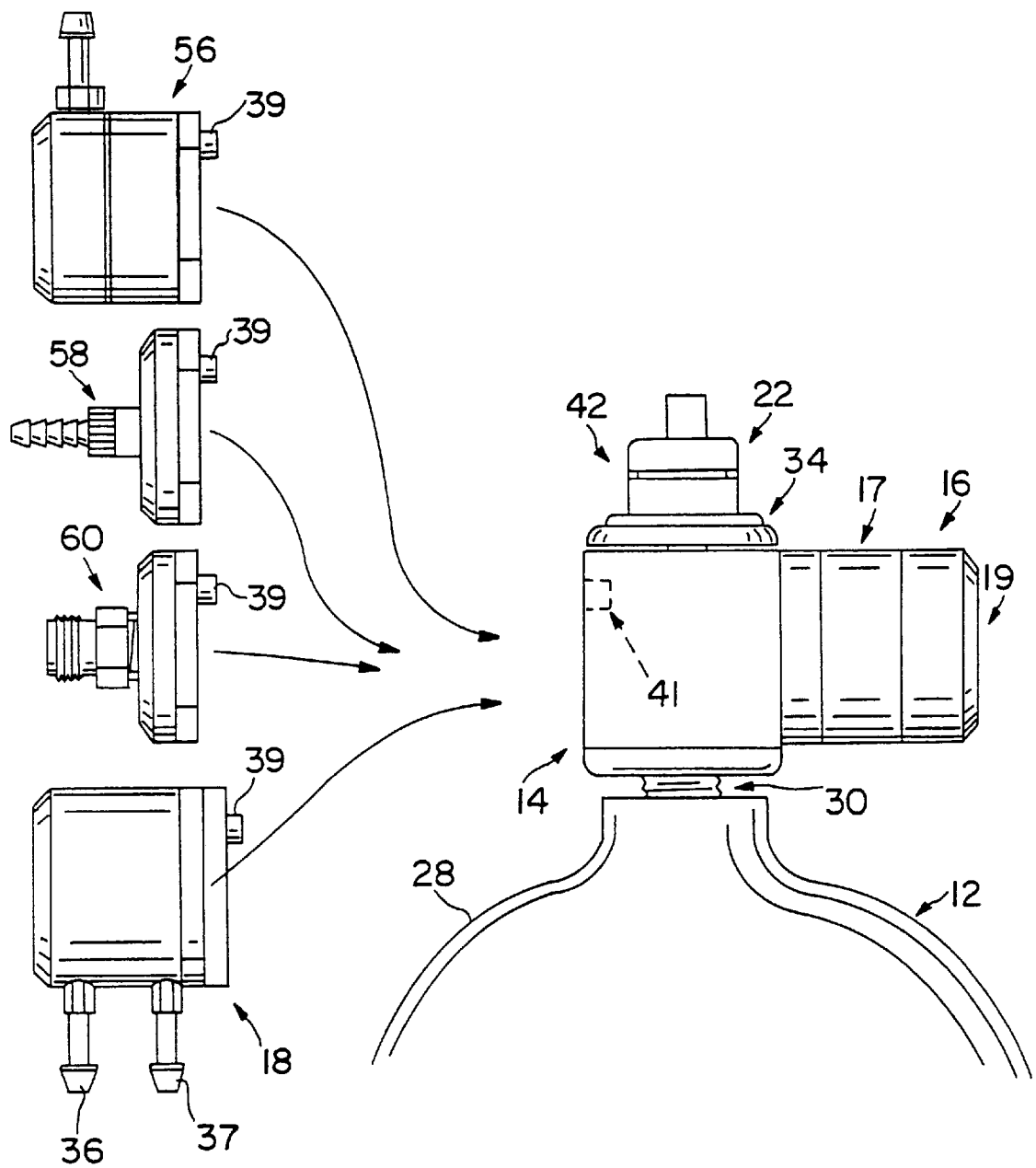
FIG. 6 is a view similar to FIG. 5 showing that other modular components can be mounted to the left side of the pressure regulator module in lieu of the pneumatic demand oxygen valve module.

A modular oxygen-conserving regulator assembly 10 of the type disclosed herein is configured to enable a healthcare service technician to replace pneumatic demand oxygen valve module 18 in oxygen-conserving regulator 10 with other modular components or units as shown, for example, in FIG. 6. For example, each of a rotatable oxygen discharge outlet unit 56, a designated flow outlet unit 58, or a DISS (i.e., Diameter-Index Safety System) unit 60 can be detachably coupled to pressure regulator module 14 using a suitable attachment mechanism in the position alternatively occupied by pneumatic demand oxygen valve module 18. This type of modular component system enables users to adapt and reconfigure oxygen-conserving regulator assembly 10 as required to suit particular oxygen therapy circumstances facing a patient.

Pressure regulator module 14 is formed to include an oxygen outlet 49 (shown, for example, in FIG. 7) for discharging low-pressure oxygen into an inlet passage 53 formed in flow controller module 16 as shown, for example, in FIGS. 2 and 7. Flow controller module 16 also includes first outlet means 46 for discharging low-pressure, metered oxygen into a horizontally extending auxiliary passageway 48 formed in regulator module 14 and coupled to demand module 18 as shown, for example, in FIGS. 2, 7, 7A, and 10–12. Also, low-pressure, metered oxygen can flow through second outlet means 50 formed in flow controller module 16 to demand module 18 through a horizontally extending patient supply passageway 51 formed in regulator module 14 as shown, for example, in FIGS. 2, 7, 7A, 8, and 10–12. In a presently preferred embodiment, passageways 48, 51 are really drilled passageways formed in pressure regulator module 14.

The design in accordance with the present invention is intended to provide a high-pressure oxygen-gas regulation system that allows the application of existing and future oxygen-conservation technology. The modular regulator concept disclosed herein would accommodate various control and outlet modules. Control modules include various ranges of flow control valves, fixed flow orifices, or variable flow-metering valves. Outlet modules would initially include barbed fittings, DISS fittings, multiple fittings, pneumatic demand device conserving devices, or various rotating fittings. Alternative outlet modules may include a pneumatic pulse conservation device or electronic control modules (pulse or feedback compensated precision flow). Customers could upgrade units or configure existing units as desired.

Provision of an integral regulator unit 10 including a pneumatic demand oxygen valve module 18, flow controller module 16, and pressure regulator module 14 as disclosed herein eliminates tubing connections between existing pulse devices and stand-alone regulators (not shown). This design, in accordance with the present invention, provides a lightweight, compact, portable oxygen-conservation system for patients in need of supplemental oxygen.

Figure 7A:
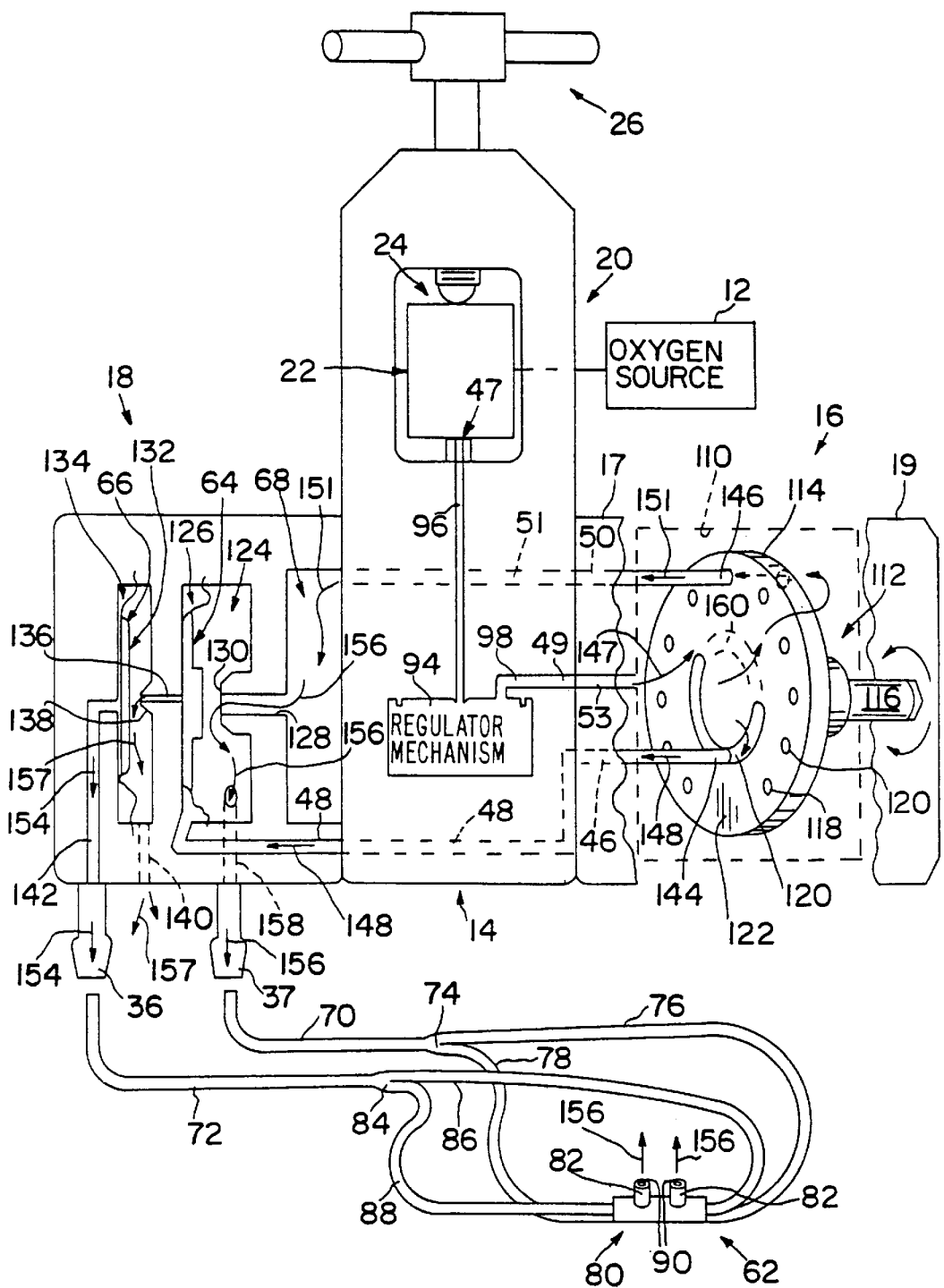
FIG. 7A is a schematic view similar to FIG. 7 showing that the diaphragm valve member will move to an opened position and the patient will receive oxygen from the oxygen supply chamber as soon as the patient begins to inhale.
Figure 8:
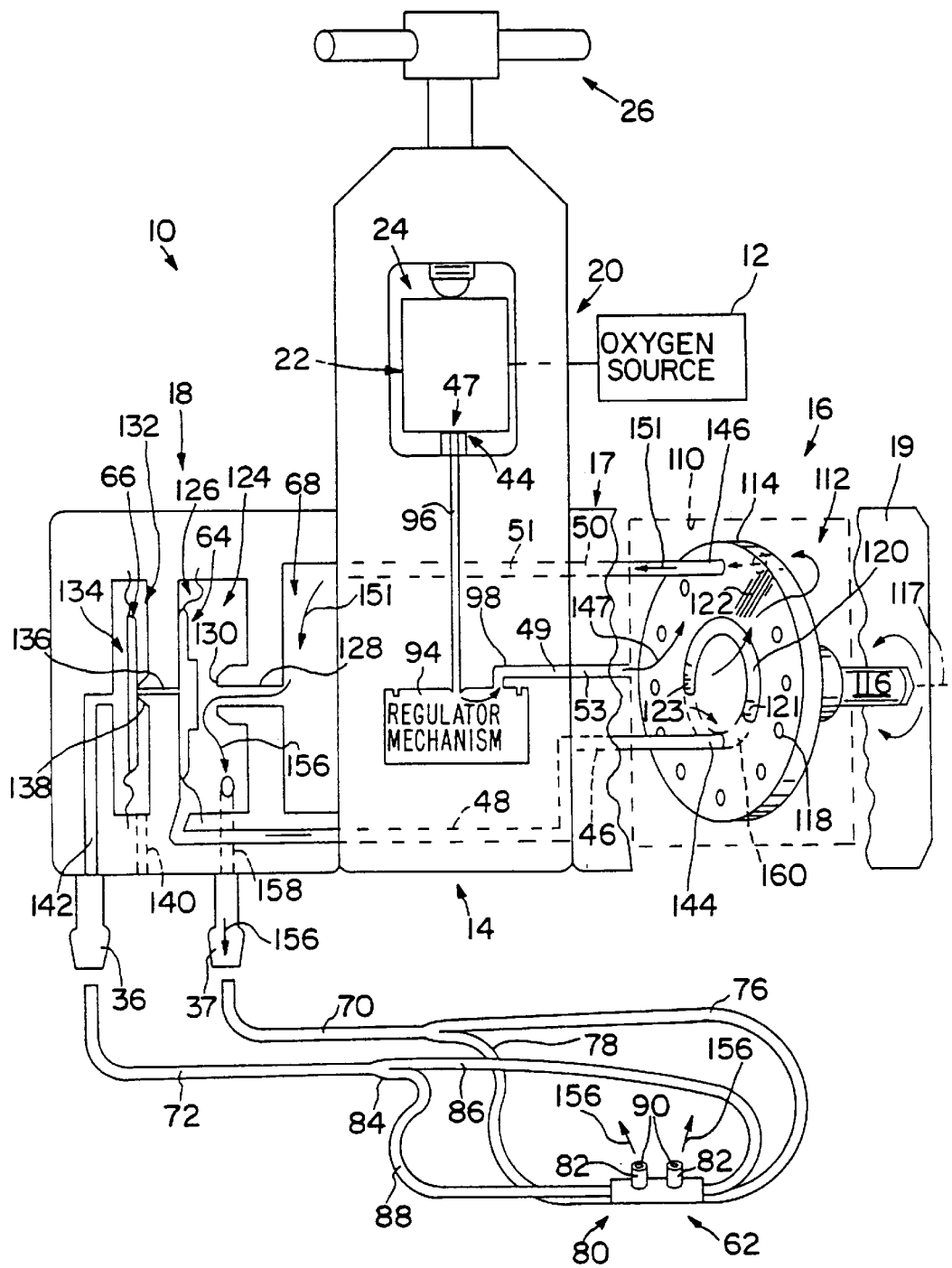
FIG. 8 is a schematic view similar to FIG. 7 showing the rotary valve positioned in a "continuous flow" mode (i.e., second position range) to block oxygen flow from the oxygen-flow controller module to the pneumatic demand valve module through the diaphragm supply passageway to "disable" the pneumatic demand valve module (by allowing the diaphragm to be moved to and retained in its opened position by pressurized oxygen flowing out of the oxygen supply chamber to the patient) and to allow "continuous" oxygen flow from the oxygen-flow controller module to the pneumatic demand valve module through the patient supply passageway so that a patient using the breathing cannula will receive oxygen when inhaling and exhaling.
Figure 9:
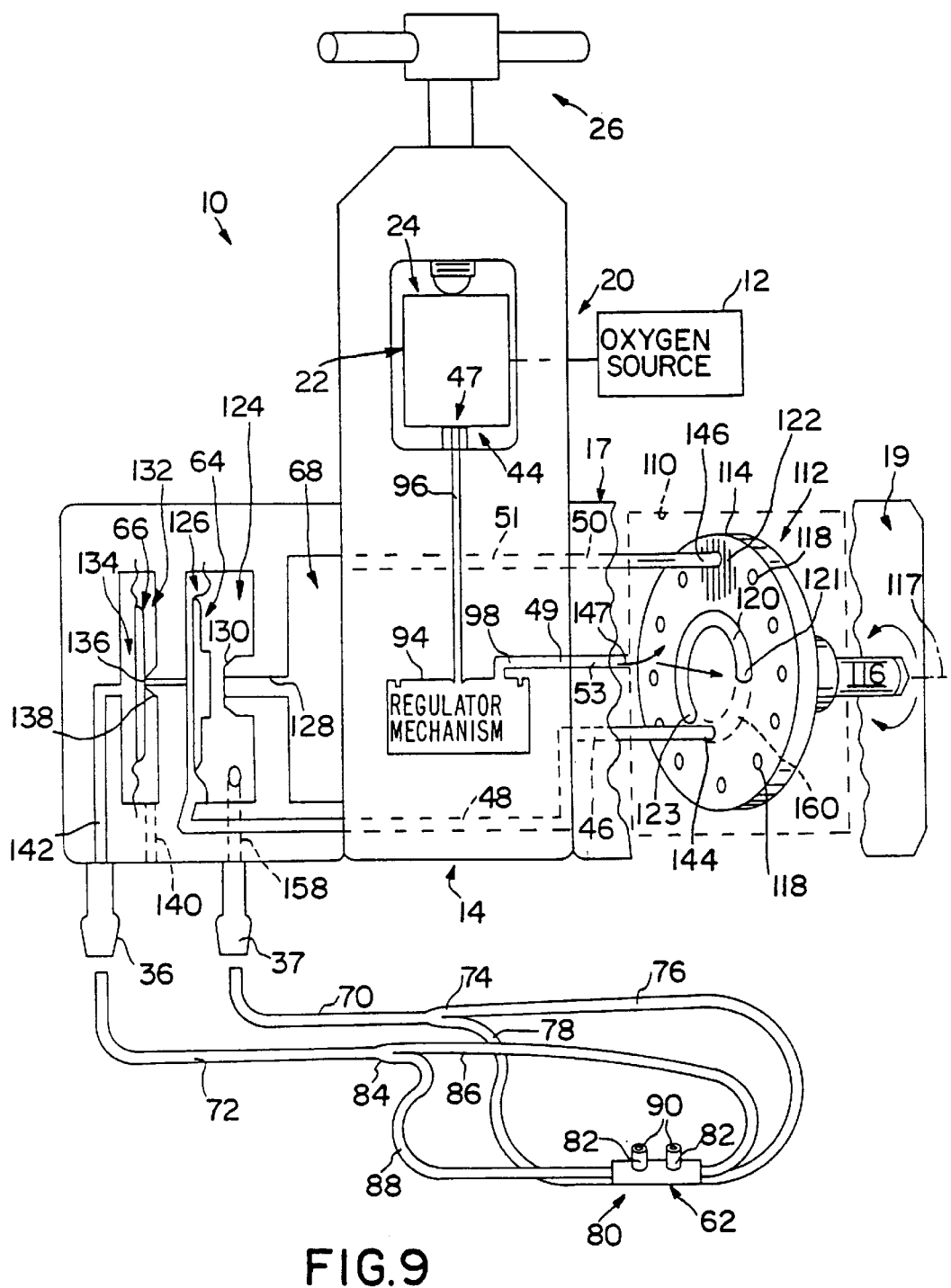
FIG. 9 is a schematic view similar to FIGS. 7 and 8 showing the rotary valve positioned in an "off" mode (i.e., third position range) to block any oxygen flow from the oxygen-flow controller module to the pneumatic demand oxygen module through both of the diaphragm and patient supply passageways formed in the regulator.

Diagrammatic illustrations of modular regulator assembly 10 are provided in FIGS. 7–9 to show how assembly 10 can be operated to control the flow of oxygen gas from high-pressure oxygen gas cylinder 12 to a patient wearing and using a breathing cannula 62. Regulator assembly 10 is functioning in "demand" mode in FIGS. 7 and 7A to deliver oxygen to a patient only when the patient breathing through cannula 62 is inhaling and in "continuous" mode in FIG. 8 to deliver oxygen continuously to the patient whether the patient is inhaling through or exhaling into cannula 62. Regulator assembly 10 is shown in its "off" mode in FIG. 9 so that no oxygen gas is flowing from cylinder 12 to cannula 62 through regulator assembly 10.

FIG. 7 shows how air exhaled by a patient into cannula 62 is transmitted through sensing port 36 to demand module 18 to cause a diaphragm valve member 64 and an inhale/exhale sensing diaphragm 66 positioned in demand module 18 to cooperate to block flow of oxygen passing through patient supply passageway 51 formed in regulator module 14 into an oxygen supply chamber 68 formed in demand module 18 from demand module 18 into cannula 62. FIG. 7A shows how the inhale/exhale sensing diaphragm 66 moves to an actuated position whenever a patient breathing through cannula 62 inhales to allow pressurized oxygen in oxygen supply chamber 68 in demand module 18 to assist in moving diaphragm valve member 64 to a venting position so that oxygen is discharged from demand module 18 into cannula 62 through gas outlet 37.

Dual lumen cannula 62 is shown diagrammatically in FIGS. 7–9. Cannula 62 includes a flexible gas supply tube 70 and a sensing tube 72. Gas supply tube 70 is coupled to gas outlet 37 on demand module 18 and adjacent to the patient divides at juncture 74 to present two branch legs 76, 78. These branch legs 76, 78 are interconnected by means of a nasal delivery structure 80 including a pair of spaced-apart gas delivery tubes 82 insertable into the nasal cavities of a patient. Sensing tube 72 is coupled to sensing port 36 on demand module 18 and adjacent to the patient divides at juncture 84 to present two branch legs 86, 88. A pair of short sensing tubes 90 are located within the spaced-apart gas delivery tubes 82 and coupled to branch legs 86, 88. The function of sensing tube 72 is to convey and transmit via short sensing tubes 90 the pressure conditions induced during the patient's breathing efforts, such pressure conditions being transmitted to inhale/exhale sensing diaphragm 66 in demand module 18 via sensing port 16.

Referring now to FIG. 7, regulator assembly 10 is shown in demand mode during patient exhaling. Breath exhaled by the patient wearing cannula 62 into the two short sensing tubes 90 provided in nasal delivery structure 80 is represented diagrammatically by two downwardly pointing arrows 92.

Pressure regulator module 14 includes a conventional internal regulator mechanism 94 coupled to oxygen inlet 47 via inlet conduit 96 and to oxygen outlet 49 via outlet conduit 98. Regulator mechanism 94 (shown in more detail in FIGS. 10–12) operates in a conventional manner to convert high pressure (e.g., 3000 psi) oxygen gas admitted through inlet conduit 96 into low pressure (e.g., 20 or 50 psi) oxygen gas suitable for use in flow controller module 16 and demand module 18 and by the patient wearing cannula 62.

Flow controller module 16 is formed to include a sealed internal chamber 110 coupled to inlet conduit 53 and first and second outlet means 46, 50. Low-pressure oxygen discharged from regulator module 14 is admitted into internal chamber 110 via inlet conduit 53. A rotary valve 112 included in flow controller module 16 includes a rotor disk 114 positioned to lie in internal chamber 110 and a drive shaft 116 fixed to rotor disk 114 and coupled to rotate with flow selector knob 19 relative to base 17. The rotor disk 114 is formed to include various oxygen flow-metering apertures 118, an oxygen flow channel 120, and a flow-shutoff plate 122. Rotary valve 112 is positioned to be moved between a first position range shown, for example, in FIGS. 7 and 7A, a second position range shown, for example, in FIG. 8, and a third position range shown, for example, in FIG. 9.

Demand module 18 is formed to include an oxygen flow chamber 124 on one side of diaphragm valve member 64 and a diaphragm biasing chamber 126 on the other side of diaphragm valve member 64. A central passage 128 conducts pressurized oxygen from oxygen supply chamber 68 into oxygen flow chamber 124 for delivery to gas outlet 37 (and cannula 62) whenever diaphragm valve member 64 is moved to disengage a valve seat 130 around central passage 128. Demand module 18 also includes a vent chamber 132 on one side of inhale/exhale sensing diaphragm 66 and a venting control chamber 134 on the other side of inhale/exhale sensing diaphragm 66. A central passage 136 conducts pressurized oxygen from diaphragm biasing chamber 126 into vent chamber 132 for discharge to the atmosphere through vent passageway 140 whenever inhale/exhale sensing diaphragm 66 is moved to disengage a valve seat 138 around central passage 136. A breath conduit 142 interconnects sensing port 36 and venting control chamber 134 in fluid communication so that a vacuum is applied to venting control chamber 134 via cannula 62, sensing port 36, and breath conduit 142 whenever a patient breathing through cannula 62 inhales.

To place regulator assembly 10 in demand mode, the user turns flow selector knob 19 in flow controller module 16 to place rotary valve 112 in a first position range so as to cause inlet 144 of first outlet means 46 to communicate with oxygen flow channel 120 formed in rotor disk 114 and inlet 146 of second outlet means 50 to communicate with one of the oxygen flow-metering apertures 118 formed in rotor disk 114 as shown in FIGS. 7 and 7A. When in demand mode, regulator assembly 10 operates to supply oxygen to the patient breathing through cannula 62 only when the patient inhales.

As shown in FIGS. 7 and 7A, low-pressure oxygen 147 discharged from regulator module 14 into flow controller module 16 is split into two flow streams in sealed internal chamber 110 by rotor disk 114 when rotary valve 112 is in the first position range so that one stream of oxygen 148 is discharged from flow controller module 16 into diaphragm supply passageway 48 formed in regulator module 14 and another stream of oxygen 151 is discharged from flow controller module 16 into patient supply passageway 51 formed in regulator module 14. As shown diagrammatically in FIGS. 7 and 7A, the one oxygen stream 148 flows from internal chamber 110 into inlet 144 of first outlet means 46 after gaining access to the open mouth of inlet 144 by first passing through a portion of oxygen flow channel 120 formed in rotor disk 114. Simultaneously, the other oxygen stream 151 flows from internal chamber 110 through a selected oxygen flow-metering aperture 118a formed in rotor disk 114 into inlet 146 of second outlet means 50.

As shown in FIG. 7, diaphragm valve member 64 in demand module 18 is retained in a closed position engaging valve seat 130 to block flow of oxygen from oxygen supply chamber 68 through central passage 128 into oxygen flow chamber 124 whenever a patient wearing cannula 62 exhales. By exhaling, the patient discharges exhaled air 152 through gas delivery tubes 82 in nasal delivery structure 80, branch legs 86, 88, sensing tube 72, sensing port 36, and breath conduit 142 to pressurize venting control chamber 134 in demand module 18 and urge inhale/exhale sensing diaphragm 66 to a closed position engaging valve seat 138 to close central passage 136. Simultaneously, the first stream of oxygen 148 discharged from flow controller module 16 passes through diaphragm supply passageway 48 to reach diaphragm biasing chamber 126 and urge diaphragm valve member 64 to a closed position engaging valve seat 130 to close central passage 128. When central passage 128 is closed, pressurized oxygen is unable to pass from oxygen supply chamber 68 out of demand module 18 through gas outlet 37. Even though exhaling air 152 from a patient is passing through gas outlet 37 into oxygen flow chamber 124, the pressure of the exhaled air 153 in chamber 124 acting on the left side of diaphragm valve member 64 does not generate a force that is great enough to move diaphragm valve member 64 from its closed position.

As shown in FIG. 7A, diaphragm valve member 64 has been moved to an opened position to allow oxygen 156 to flow to a patient wearing cannula 62 from oxygen supply chamber 68 in demand module 18 through central passage 128, oxygen flow chamber 124, oxygen discharge channel 158, gas outlet 37, gas supply tube 70, leg branches 76, 78, and gas delivery tubes 82 in nasal delivery structure 80. Diaphragm valve member 64 is able to move to an opened position as shown in FIG. 7A because pressurized oxygen extant in diaphragm biasing chamber 126 is discharged to the atmosphere through central passage 136, vent chamber 132, and vent passageway 140. Because the patient is now inhaling (and drawing air 154 out of venting control chamber 134), the sensing diaphragm 66 is free to move to an opened position under a force generated by pressurized oxygen 157 escaping diaphragm biasing chamber 126 through central passage 136.

To place regulator assembly 10 in continuous mode, the user turns flow selector knob 19 (about axis of rotation 117 relative to base 17) to the position shown diagrammatically in FIG. 8 to place rotary valve 112 in a second position range so as to cause inlet 144 of first outlet means 46 to engage only a flat wall portion 160 (extending between opposite ends 121, 123 of oxygen flow channel 120) of rotor disk 114 so that inlet 144 does not communicate with the C-shaped oxygen flow channel 120 formed in rotor disk 114. When rotor disk 114 is in this position, no oxygen is able to flow out of internal chamber 110 formed in flow controller module 16 into diaphragm supply passageway 48 to reach diaphragm biasing chamber 126 because inlet 144 searingly engages flat wall portion 160 of rotor disk 114. As a result, there is insufficient oxygen pressure extant in diaphragm biasing chamber 126 to act on the diaphragm valve member 64 and generate a force sufficient to move diaphragm valve member 64 to a closed position and thus diaphragm valve member 64 remains open continuously to allow continuous oxygen flow 156 from oxygen supply chamber 68 in demand module 18 to a patient breathing through cannula 62 via central passage 128, oxygen flow chamber 124, oxygen discharge channel 158, gas outlet 37, and cannula 62.

To place regulator assembly 10 in off mode, the user turns flow selector knob 19 (about axis of rotation 117 relative to base 17) in flow controller module 16 to place rotary valve 112 in a third position range so as to cause (1) inlet 144 of first outlet means 46 to engage only flat wall portion 160 of rotor disk 114 so that inlet 144 does not communicate with the C-shaped oxygen flow channel 120 formed in rotor disk 114 (and hence oxygen extant in chamber 110) and (2) inlet 146 of second outlet means 50 to engage only flow-shutoff plate 122 on rotor disk 114 so that inlet 146 does not communicate with any one of the oxygen flow-metering apertures 118 formed in rotor disk 114. As a result, no oxygen is discharged from internal chamber 110 in flow controller module 16 through the diaphragm and patient supply passageways 48, 51 formed in regulator module 14 toward the demand module 18 and the regulator assembly 10 is inactive.

Figure 10:
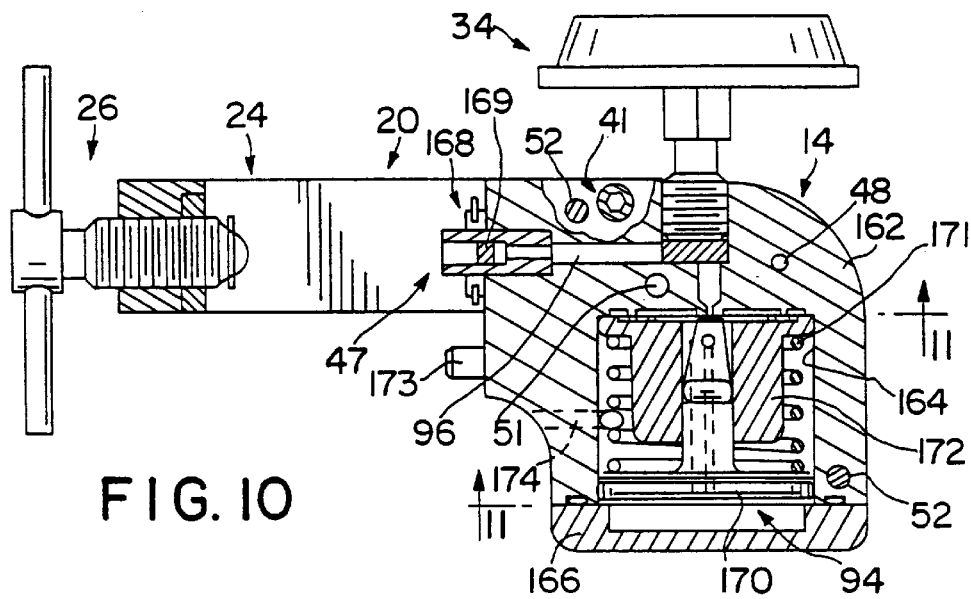
FIG. 10 is a transverse sectional view of the pressure regulator module of FIG. 2.
Figure 11:
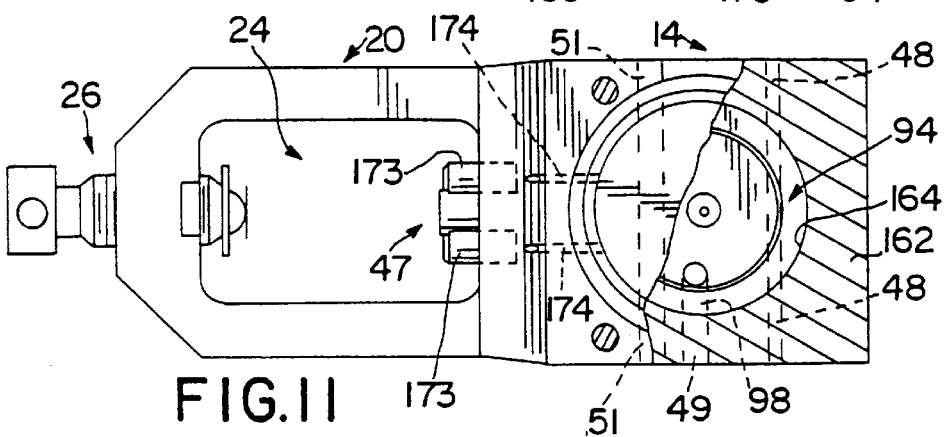
FIG. 11 is a bottom view of the pressure regulator module taken along lines 11—11 of FIG. 10.
Figure 12:
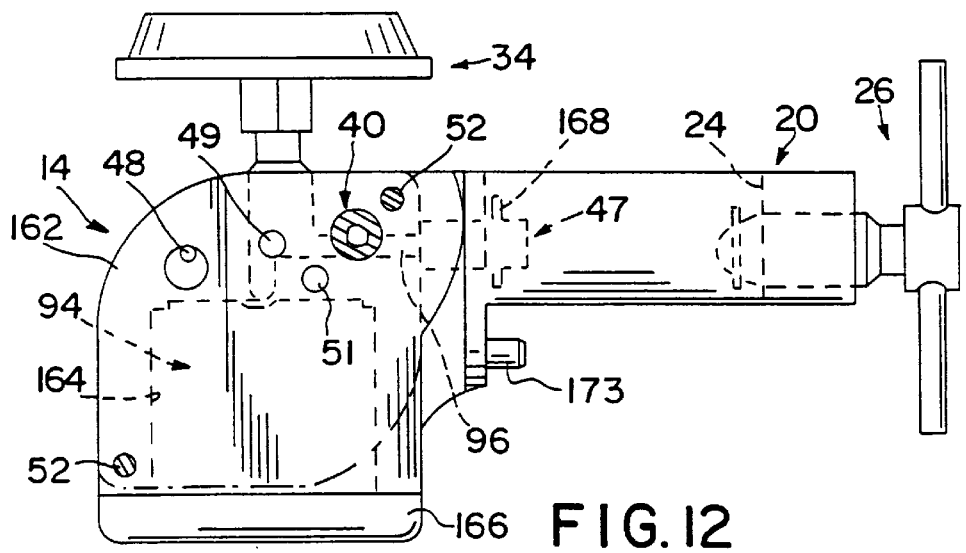
FIG. 12 is an elevational view of the right side of the pressure regulator module of FIG. 2 taken from line 12—12 of FIG. 2 looking toward the pressure regulator.

Referring now to FIGS. 10–12, regulator module 14 includes a regulator body 162 formed to include a chamber 164 containing regulator mechanism 94 and an end cap 166 closing chamber 164. A seal assembly 168 is positioned inside oxygen inlet 47. Regulator mechanism 94 is a conventional design and includes a piston 170, a spring 171, and a relief valve assembly 172. Groove pins 173 are aligned with inlet 47 and register regulator body 162 to post valve 22 when regulator module 14 is mounted on post valve 22. Regulator body 162 includes two vent passageways 174 communicating with chamber 164 and operating to vent excess pressure from chamber 164. A seal assembly 168 is positioned around oxygen inlet 47 and a filter 169 is positioned inside oxygen inlet 47.

Figure 15:
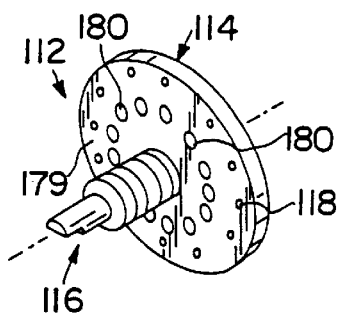
FIG. 15 is a perspective view of the rotary valve of FIG. 14 taken from the "rear" showing an inner ring of detent-receiving circular depressions and an outer ring of flow passage inlets formed in a rear face of the rotor in the rotary valve.
Figure 14:
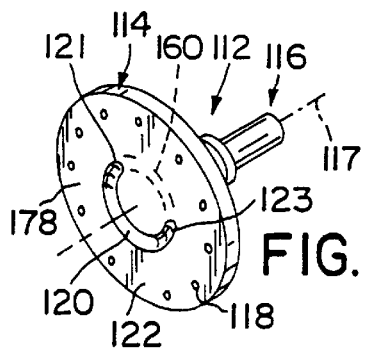
FIG. 14 is a perspective view of the rotary valve included in the oxygen-flow controller module taken from the "front" showing a C-shaped groove and a surrounding ring of flow passage outlets formed in a front face of the rotor in the rotary valve.

Flow controller module 16 and rotary valve 112 are shown in FIGS. 13–17. The left-side face 175 of module 16 carries a mounting orientation post 38 for engaging a post receptacle 40 formed in regulator module 14 and a sealing ring 176 for surrounding an opening 177 of first outlet means 46. Front face 178 of rotor disk 114 includes an outlet opening for each of the oxygen flow-metering apertures 118 as shown in FIG. 14 and rear face 179 of rotor disk 114 includes an inlet opening for each of apertures 118 as shown in FIG. 15. Each aperture 118 includes a conventional flow restriction passage of a predetermined internal diameter therein as shown, for example, in FIG. 16 to regulate the flow rate of oxygen passing therethrough. A user selects a desired flow rated by turning rotary valve 112 about axis 117 to place the oxygen flow-metering aperture 118 having the desired internal diameter in communication with the inlet 44 of the first outlet means 46 in flow controller module 16 so that low-pressure oxygen gas is discharged from internal chamber 110 into first outlet means 46 through the selected oxygen flow-metering aperture 118 at a selected flow rate (typically measured in liters per minute).

As shown in FIG. 14, front face 178 of rotor disk 114 includes a C-shaped oxygen flow channel 120 having opposite ends 121, 123 and an "arcuate" flat wall portion 160 extending between opposite ends 121, 123 of channel 120. Front face 178 also includes a surrounding ring of outlet openings for apertures 118 and a flow-shutoff plate 122 located between two of the outlet openings for apertures 118.

As shown in FIG. 15, rear face 179 of rotor disk 114 includes an inner ring of circumferentially spaced-apart detent-receiving circular depressions 180 for receiving a ball 181 loaded by a spring 182 (see FIG. 16) to fix rotor disk 114 in one of several predetermined positions following rotation of flow selector knob 19 about axis 117 to a selected flow-metering position. Rear face 179 also includes an outer ring of inlet openings for apertures 118.

Figure 16:
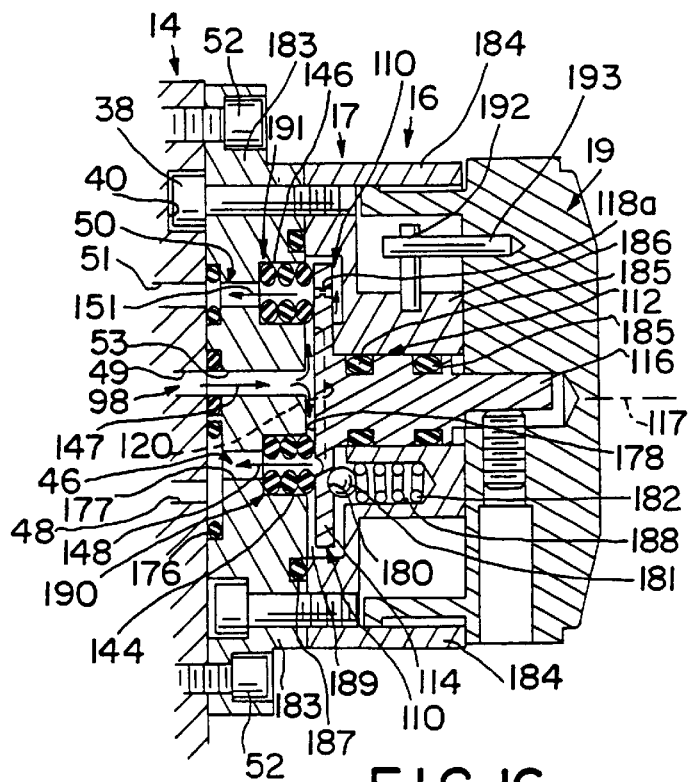
FIG. 16 is a sectional view of the oxygen-flow controller module taken along line 16—16 of FIG. 13 showing a housing formed to include a chamber containing the rotor included in the rotary valve, one oxygen input channel for introducing oxygen into the chamber formed in the housing, and two oxygen output channels for receiving oxygen that has been "metered" in the chamber by the rotor to a selected flow rate (liters per minute) and discharging the metered oxygen from the chamber to both of the diaphragm and patient supply passageways formed in the pressure regulator module.

Base 17 in flow controller module 16 includes a mounting plate 183 for mounting on regulator module 14 and an interface plate 184 interposed between mounting plate 183 and rotatable flow selector knob 19 as shown best in FIG. 16. Mounting plate 183, interface plate 184, and drive shaft 116 of rotary valve 112 cooperate to define sealed internal chamber 110 within flow controller module 16 as shown, for example, in FIG. 16. Two O-ring seals 185 engage drive shaft 116 and a central portion 186 of interface plate 184 and a single O-ring seal 187 lies in an annular groove formed in mounting plate 183 and engages interface plate 184. Rotor disk 114 is positioned by drive shaft 116 to lie wholly within sealed internal chamber 110 as the flow selector knob 19 is turned by a user to rotate rotary valve 112 about axis 117 between the first, second, and third position ranges.

A detent mechanism is mounted in central portion 186 of interface plate 184 to project toward and engage circular depressions 180 formed in rear face 179 of rotor disk 114 to fix the position of rotary valve 112 in one of several predetermined fixed positions within base 17 of flow controller module 16. The detent mechanism includes ball 181 and compression spring 182 positioned to lie in a channel 188 formed in central portion 186 of interface plate 184 and open toward rear face 179 of rotor disk 114. Spring 182 yieldably urges ball 181 away from interface plate 184 to engage a circular depression 180 formed in rear face 179 whenever rotor disk 114 is rotated to a predetermined position matching either an oxygen flow-metering orifice 118 or flow-shutoff plate 122 in communication with the inlet 146 of the second outlet means 50 of flow controller module 16.

As shown in FIG. 16, front face 178 of rotor disk 114 is supported for rotation about axis 117 in spaced-apart relation to surface 189 of mounting plate 183 by two stacks 190, 191 of O-ring seals. A first O-ring seal stack 190 is mounted in inlet 144 of first outlet means 46 as shown, for example, in FIG. 16 to rotatably support and sealingly engage front face 178 of rotor disk 114. A second O-ring seal stack 191 is mounted in inlet 146 of second outlet means 50 as shown, for example, in FIG. 16 to rotatably support and sealingly engage front face 178 of rotor disk 114. Essentially, rotor disk 114 "floats" in interior chamber 110 so that low-pressure oxygen gas 147 discharged into interior chamber 110 from regulator module 14 through inlet passage 53 and "surrounds" rotor disk 114.

Stop posts 192, 193 are positioned in flow controller module 16 to limit rotation of flow selector knob 19 relative to base 17 to less than 360°. Stop post 192 is fixed to central portion 186 of interface plate 184 and arranged to extend in a radially outward direction away from axis of rotation 117. Stop post 193 is fixed to flow selector knob 19 and arranged to extend in spaced-apart parallel relation to axis 117 in a direction toward regulator module 14 so as to engage stop post 192 at some point during rotation of flow selector knob 19 in either direction about axis of rotation 117.

Figure 17:
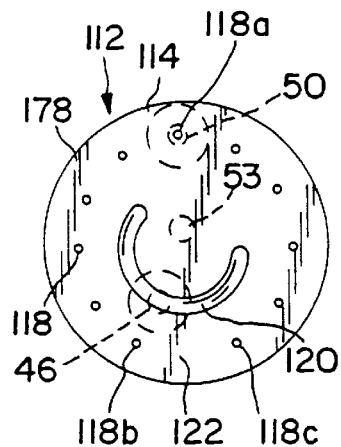
FIG. 17 is an elevational view of the front face of the rotor that is shown diagrammatically in FIGS. 7–9 and illustratively in FIGS. 14–16.

Referring now to FIG. 17, in a currently preferred embodiment, oxygen flow-metering apertures 118 are sized so that aperture 118b is sized to include the greatest flow restriction (i.e., smallest internal diameter) to produce a minimum oxygen flow rate (e.g., 0.5 liters/minute) to a patient when matched with inlet 146 of second outlet means 50. Oxygen flow-metering aperture 118c is sized to include the smallest flow restriction (i.e., largest internal diameter) to produce a maximum oxygen flow rate (e.g., 6.0 liters/minute) to a patient when matched with inlet 146.

Figure 18:
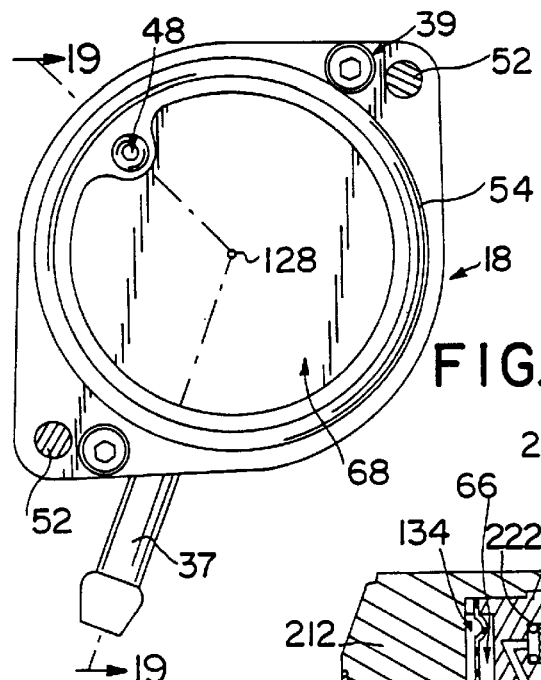
FIG. 18 is an elevational view of the right side of the pneumatic demand valve module taken from line 18—18 of FIG. 2 looking toward the pneumatic demand valve module.
Figure 19:
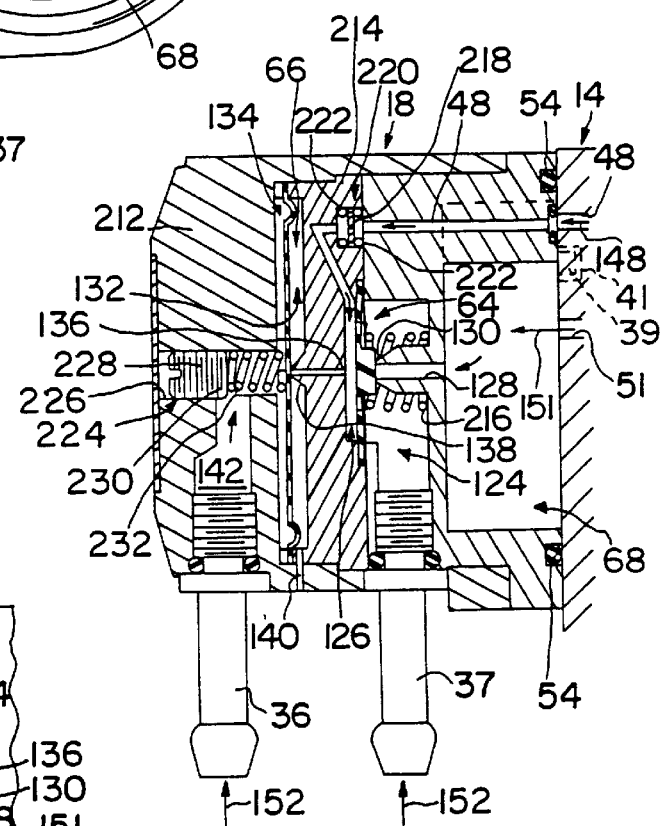
FIG. 19 is a sectional view of the pneumatic demand valve module taken along line 19—19 of FIG. 18 showing that no oxygen flows from the oxygen supply chamber in the pneumatic demand valve module to the patient as the patient exhales because oxygen supplied through the diaphragm supply passage pressurizes the biasing chamber in the pneumatic demand valve module to urge the diaphragm valve member to a closed position.
Figure 20:
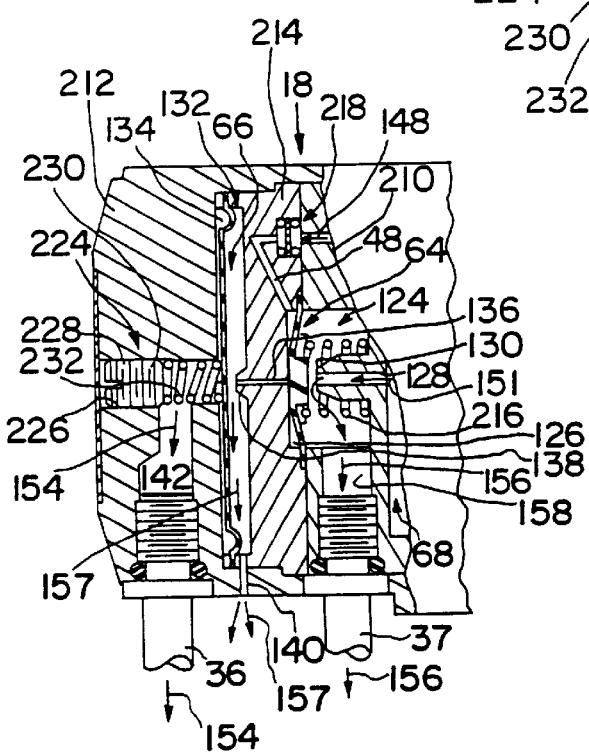
FIG. 20 is a view similar to FIG. 19 showing that oxygen flows from the oxygen supply chamber to the patient during patient inhaling because a separate inhale/exhale sensing diaphragm moves to vent pressurized oxygen in the biasing chamber so that the diaphragm valve member is moved by a spring and pressurized oxygen in the oxygen supply chamber to an opened, oxygen-supply position.
Figure 25:
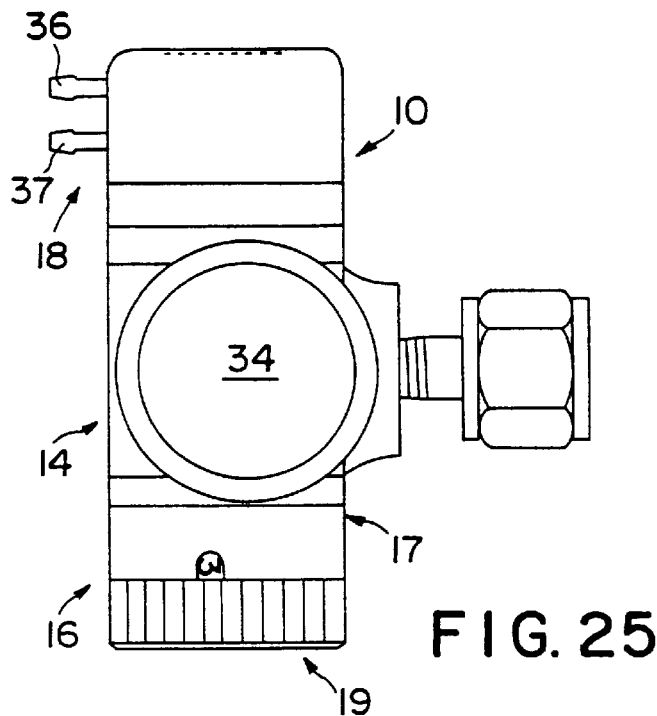
FIG. 25 is a plan view of an alternative embodiment of a regulator assembly in accordance with the invention configured to include a nut and tailpiece connector.
Figure 26:
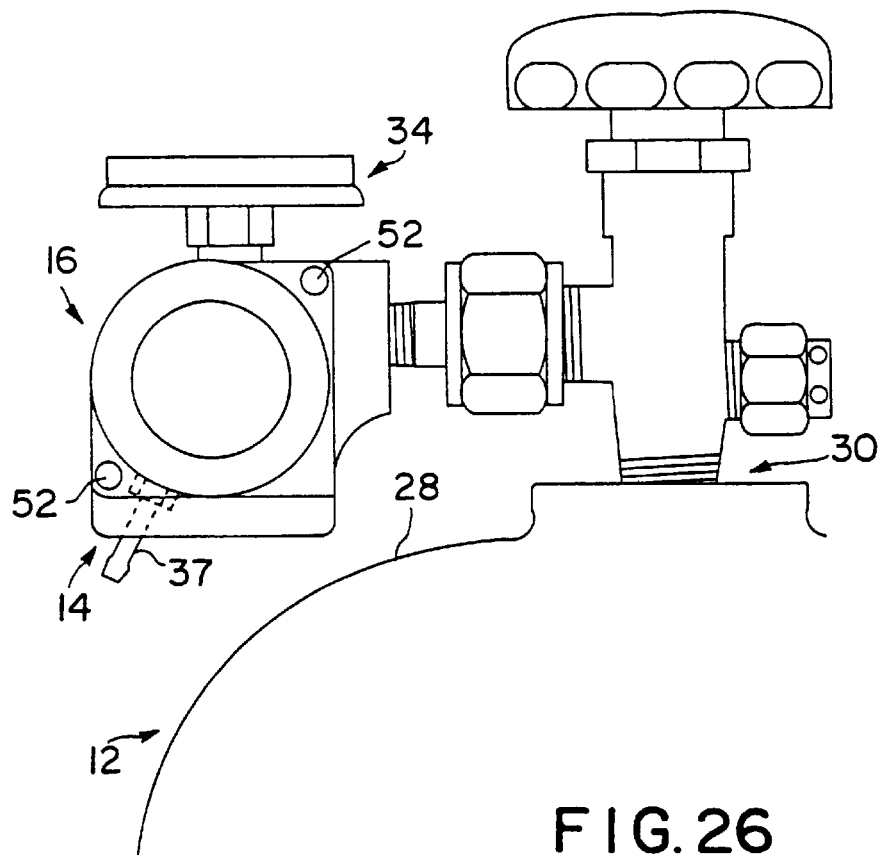
FIG. 26 is a side elevation of the regulator assembly of FIG. 25 mounted on an oxygen tank.

A presently preferred embodiment of demand valve module 18 is shown in FIGS. 18–20. A description of a suitable pneumatic demand oxygen valve is included in U.S. Pat. No. 5,360,000, which description is incorporated by reference herein.

Preferably, the pneumatic demand valve contained in demand module 18 includes a valve body presenting a gas flow passageway, together with pneumatically coupled sensing and slave diaphragms 66, 64. The sensing diaphragm 66 is a differential pressure diaphragm mounted in a chamber in the valve body and exposed to patient breathing inputs and other pressure inputs. The slave diaphragm is a diaphragm valve member 64 that is interposed in the flow passageway and prevents gas flow during the exhalation phases of the patient's breathing cycle. During inhalation sensed by the sensing diaphragm 66, the slave diaphragm valve member 64 is shifted to open the gas flow passageway in the valve, thus permitting passage of gas to the patient through cannula 62.

Referring now to FIG. 19, demand module 18 includes a mounting plate 210 carrying mounting orientation post 39, a housing 212, and a central body 214 trapped between mounting plate 210 and housing 212. Mounting plate 210 is coupled to regulator module 14 and an O-ring seal 54 is used to establish a seal between mounting plate 210 and regulator module 14.

A biasing spring 216 is positioned in oxygen flow chamber 124 to surround central passage 128. One end of spring 216 engages mounting plate 210 and an opposite end of spring 216 engages diaphragm valve member 64. Spring 216 yieldably urges diaphragm valve member 64 in a direction away from engagement with valve seat 130.

A removable, drop-in, apertured disk 218 is placed in a chamber 220 formed in central body 214 to lie in diaphragm supply passageway 48. O-ring seals 222 are positioned in chamber 220 on opposite sides of apertured disk 218 to block flow of pressurized oxygen in passageway 48 around disk 218. Apertured disk 218 is formed to include a central aperture defining means for reducing the flow rate of pressurized oxygen delivered to diaphragm biasing chamber 126 through diaphragm supply passageway 48. Disk 218 is removable so that the flow rate of oxygen to diaphragm biasing chamber 126 can be changed simply by disassembling regulator module 18, removing disk 218 from chamber 220, and dropping another disk having a desired flow-rate characteristic (e.g., central aperture size) in chamber 220.

Sensitivity adjustment means 224 is provided in housing 212 for selectively and positively bringing the inhale/exhale sensing diaphragm 66 and vent valve seat 138 closer together so that the precise location of the vent valve seat 138 relative to the sensing diaphragm 66 can be varied. As shown in FIGS. 19 and 20, housing 212 includes a bore 226 that is internally threaded and communicated with inhale/exhale sensing diaphragm 66. A threaded member 228 is received in bore 226 and terminates in a tip 230. A compression spring 232 positioned in bore 226 has one end engaging tip 230 and an opposite end engaging sensing diaphragm 66. Threaded member 228 is rotatable in bore 226 so as to provide a sensitivity adjustment, i.e., the precise location of inhale/exhale sensing diaphragm 66 relative to vent valve seat 138 can be varied by rotating member 228 to adjust load on compression spring 232 engaging inhale/exhale sensing diaphragm 66.

During the exhalation phase of operation illustrated in FIG. 19, the pressure conditions within venting control chamber 134 maintain inhale/exhale sensing diaphragm 66 in engagement with seat 138. When the patient inspires, the negative pressure within venting control chamber 134 causes sensing diaphragm 66 to lift as shown in FIG. 20, whereby biasing gas 157 within chamber 132 passes to the atmosphere through communicating passageway 140. This creates an inequality of forces on the diaphragm valve member 64, whereby the latter is lifted thus opening the gas flow passageway 128 so that gas may pass through chamber 124, path 158, and ultimately out the gas outlet 37 to the patient wearing cannula 62.

It will be seen that the inhale/exhale sensing diaphragm 66 and diaphragm valve member 64 are pneumatically coupled for operation of the diaphragm valve member 64 in response to movement of the sensing diaphragm 66; the latter is in turn moved in response to the patient's breathing efforts as transmitted through the cannula 62.

A very desirable feature of the invention results from its fail-safe characteristics. Specifically, a fail-safe demand device is one that, upon a mechanical failure of one or more components, establishes a continuous flow of oxygen to be delivered to the recipient at the prescribed rate.

An alternative demand module 318 is shown in FIGS. 21 and 22. This demand module 318 is the same as demand module 18 except that it includes a "demand/continuous" flow selector switch 340 in communication with diaphragm supply passageway 48. Thus, it is not necessary to use a flow controller module like module 16 which is configured to regulate flow of oxygen through diaphragm supply passageway 48 by rotating flow selector knob 19 to position inlet 144 of first outlet means 46 in communication with either (1) oxygen flow channel 120 formed in rotor disk 114 to allow oxygen to flow from interior chamber 110 into inlet 144 or (2) flat wall portion 160 on rotor disk 114 to block flow of oxygen from interior chamber 110 into inlet 144.

A system is provided inside pneumatic demand oxygen valve 318 to control the "mode of distribution" of oxygen flow from the pneumatic demand oxygen valve to a patient. This system is shown in FIGS. 21 and 22 and is controlled by a pulse/continuous oxygen flow switch 340. This switch 340 gives a healthcare provider or the patient the option to distribute pulsed oxygen flow or continuous oxygen flow to the patient as controlled by the pneumatic demand oxygen valve 318.

As shown in FIG. 22, flow switch 340 includes a switch plate 342, tab 344, grip portion 346, and exhaust 354. A user can slide grip portion 346 relative to housing 212 in direction 348 to the position shown in FIG. 22 to cause switch plate 342 to move to a position blocking flow of low-pressure oxygen 148 in diaphragm supply passageway 48 to diaphragm biasing chamber 126. Alternatively, a user can slide grip portion 346 relative to housing 212 in direction 350 to another position (not shown) placing an aperture 352 formed in switch plate 342 in line with diaphragm supply passageway 48 to allow flow of oxygen through diaphragm supply passageway 48 toward diaphragm biasing chamber 126.

It is within the scope of the present invention disclosed herein to use regulator assembly 10 in connection with other gases such as nitrogen. Other gases or applications may benefit from a modular regulator assembly of the type disclosed herein. For example, nitric oxide therapy is needed for impaired patients and there may be a use for regulator assembly 10 in that context.

At the present time, regulator assembly 10 preferably includes a pneumatic device. It is within the scope of the present invention to include an electronics valve device. Continuous flow following the initial precharge bolus may also be truncated but not at the present time.

As shown in FIG. 23, oxygen-flow controller module 16 can be coupled to one side of regulator module 14 using bolts 52 passing through apertures formed in module base 17 and regulator module 14 and using a mounting orientation post 38 (see FIG. 13) coupled to module base 17 and configured to fit in a post-receiving aperture 40 formed in regulator module 14 (see also FIG. 16). Use of mounting orientation post 38 and post-receiving aperture 40 operates to align all openings formed in oxygen-flow controller module 16 with companion openings formed in regulator module 14 as shown, for example, in FIG. 16.

As shown in FIG. 24, pneumatic demand valve module 18 can be coupled to another side of regulator module 14 using bolts 52 passing through apertures formed in mounting plate 210 and regulator module 14 and using a mounting orientation post 39 (see FIG. 18) coupled to mounting plate 210 and configured to fit in a post-receiving aperture 41 formed in regulator module 14 (see also FIG. 19). Use of mounting orientation post 39 and post-receiving aperture 41 operate to align all openings formed in a pneumatic demand valve module 18 with companion openings formed in regulator module 14 as shown, for example, in FIG. 19.

Although the invention has been described in detail with reference to preferred embodiments, variations and modifications exist within the scope and spirit of the invention as described and defined in the following claims.

We claim:

1. Apparatus for controlling discharge of oxygen from an oxygen supply source to a patient, the apparatus comprising
   an oxygen supply inlet,
   a pressure regulator coupled to the oxygen supply inlet and configured to reduce pressure of oxygen received from the oxygen supply inlet to a selected magnitude,
   a flow controller coupled to the pressure regulator to position the pressure regulator between the oxygen supply inlet and the flow controller and configured to meter oxygen received from the pressure regulator at a selected flow rate, and
   an oxygen distribution assembly including a pneumatic demand oxygen valve and a conduit conducting oxygen discharged from the flow controller to the pneumatic demand oxygen valve for delivery to a patient, the pressure regulator being positioned to lie between the flow controller and the pneumatic demand oxygen valve.

2. The apparatus of claim 1, wherein the pressure regulator includes a regulator body and a regulator mechanism positioned to lie in the regulator body and receive oxygen from the oxygen supply inlet and the regulator body is formed to include a portion of the conduit so the oxygen discharged from the flow controller passes through the regulator body before said oxygen is admitted into the pneumatic demand oxygen valve.

3. The apparatus of claim 2, wherein the pneumatic demand oxygen valve includes a valve body formed to include a patient supply passageway having a gas inlet coupled to the conduit and a gas outlet for attachment to a breathing line and a diaphragm valve member movable to open and close the patient supply passageway and the oxygen distribution assembly further includes an auxiliary conduit conducting oxygen from the flow controller to the diaphragm valve member to move the diaphragm valve member to a position closing the patient supply passageway.

4. The apparatus of claim 3, wherein the regulator body is formed to include a portion of the auxiliary conduit.

5. The apparatus of claim 3, wherein the flow controller includes a flow controller housing formed to include an internal chamber coupled to the conduit and to the auxiliary conduit, a passageway conducting oxygen from the pressure regulator to the internal chamber, and a flow control valve positioned in the internal chamber for movement relative to the flow controller housing between a first position range communicating oxygen from the internal chamber though the conduit and the auxiliary conduit to the diaphragm valve member, a second position range communicating oxygen from the internal chamber though the conduit to the diaphragm valve member without flowing oxygen through the auxiliary conduit to the diaphragm valve member, and a third position range blocking flow of oxygen in the internal chamber to the diaphragm valve member through the conduit and the auxiliary conduit.

6. The apparatus of claim 3, wherein the flow controller includes a flow controller housing coupled to the regulator body and formed to include an internal chamber coupled to the conduit and a flow control valve positioned in the internal chamber for movement relative to the housing to control discharge of oxygen from the internal chamber into the conduit and the pneumatic demand oxygen valve includes a valve body coupled to the regulator body and formed to include a patient supply passageway having a gas inlet coupled to the conduit and a gas outlet for attachment to a breathing line and a valve member movable relative to the valve body to open and close the patient supply passageway.

7. The apparatus of claim 6, wherein the regulator body includes a first external surface facing in one direction and a second external surface facing in another direction, the flow controller housing is coupled to the first external surface, and the valve body is coupled to the second external surface.

8. The apparatus of claim 1, wherein the conduit includes an inlet end coupled to the flow controller, an outlet end coupled to the pneumatic demand oxygen valve, and a middle portion interconnecting the inlet and outlet ends and passing through the regulator body of the pressure regulator.

9. The apparatus of claim 1, wherein the pressure regulator includes a regulator body receiving oxygen from the oxygen supply inlet and a regulator mechanism regulating pressure of oxygen received in the regulator body and the pneumatic demand oxygen valve includes a valve body coupled to the regulator body and formed to include a patient supply passageway having a gas inlet for attachment to the conduit and a gas outlet adapted for attachment to a breathing line and a valve seat in the patient supply passageway and a valve member for engaging and disengaging the valve seat to control flow of gas inlet to the gas outlet through the patient supply passageway.

10. The apparatus of claim 9, wherein the regulator body is formed to include a portion of the conduit.

11. The apparatus of claim 10, wherein the valve member includes a first wall facing away from the valve seat and a second wall facing toward the valve seat, the oxygen distribution assembly further includes an auxiliary conduit conducting oxygen from the flow controller to the first wall of the valve member, the valve body is formed to cause the patient supply passageway to conduct oxygen to the second wall of the valve member, and the regulator body is also formed to include a portion of the auxiliary conduit.

12. The apparatus of claim 9, wherein the pneumatic demand oxygen valve further includes a differential pressure controller positioned to lie in the valve body and configured to communicate with the auxiliary conduit and move the valve member from a closed position against the valve seat to an opened position away from the valve seat in response to inhalation of a patient breathing through the gas outlet.

13. The apparatus of claim 9, wherein the flow controller includes means for splitting the flow of oxygen received from the pressure regulator into a first oxygen stream discharged into the conduit and conducted through the patient supply passageway to reach a first side of the valve member facing toward the valve seat and a second oxygen stream conducted through an auxiliary conduit formed in the regulator body to reach a second side of the valve member facing away from the valve seat.

14. The apparatus of claim 1, wherein the flow controller includes a housing formed to include an internal chamber coupled to the conduit and a passageway conducting oxygen from the pressure regulator to the internal chamber and a flow control valve extending into the internal chamber and moving therein to regulate oxygen flow from the internal chamber into the conduit.

15. The apparatus of claim 14, wherein the flow control valve includes a rotor disk positioned in the internal chamber to receive oxygen discharged into the internal chamber through the passageway formed in the pressure regulator and a shaft mounted in the housing to support the rotor disk for rotational movement in the internal chamber about an axis of rotation.

16. The apparatus of claim 15, wherein the rotor disk includes a plurality of oxygen flow-metering apertures conducting oxygen from the internal chamber into the conduit at selected flow rates and at selected rotated positions of the rotor disk around the axis of rotation relative to the housing.

17. The apparatus of claim 1, wherein the oxygen distribution assembly further includes an auxiliary conduit, the pneumatic demand oxygen valve includes valve means for controlling flow of oxygen from the conduit to the patient and an inhale/exhale sensing diaphragm pneumatically coupled to the valve means, the valve means is fluidly coupled to the auxiliary conduit, the flow controller includes a housing formed to include an internal chamber and a passageway conducting oxygen from the pressure regulator to the internal chamber and a flow control valve extending into the internal chamber, and the flow control valve is formed to include an oxygen flow channel to conduct oxygen from the internal chamber into the auxiliary conduit upon movement of the flow control valve to a predetermined position in the internal chamber communicating the auxiliary conduit to the oxygen flow channel so that oxygen is communicated through the auxiliary conduit to the valve means.

18. The apparatus of claim 17, wherein the pressure regulator includes a regulator body formed to include a portion of the auxiliary conduit.

19. The apparatus of claim 18, wherein the pressure regulator includes a regulator body formed to include a portion of the conduit.

20. The apparatus of claim 17, wherein the flow control valve is also formed to include a flat wall portion to block oxygen from flowing from the internal chamber into the auxiliary conduit upon movement of the valve to another predetermined position in the internal chamber.

21. The apparatus of claim 17, wherein the flow control valve includes a rotor disk and a shaft supporting the rotor disk for rotational movement in the internal chamber about an axis of rotation and the oxygen flow channel has an arcuate shape.

22. The apparatus of claim 21, wherein the rotor disk further includes a plurality of oxygen flow-metering apertures surrounding the arcuate oxygen flow channel.

23. The apparatus of claim 21, wherein the flow controller further includes a flow selector knob coupled to the shaft and supported to rotate about the axis of rotation relative to the housing between a first position range placing the oxygen flow channel in communication with the auxiliary conduit to allow oxygen to flow from the internal chamber into the auxiliary conduit to reach the valve means in the pneumatic demand oxygen valve and a second position range placing flat wall portion in communication with the auxiliary conduit to block oxygen from flowing from the internal chamber into the auxiliary conduit toward the valve means.

24. Apparatus for controlling discharge of oxygen from an oxygen supply source to a patient, the apparatus comprising
an oxygen supply inlet,
a pressure regulator coupled to the oxygen supply inlet and configured to reduce pressure of oxygen received from the oxygen supply inlet to a selected magnitude,
a flow controller coupled to the pressure regulator and configured to meter oxygen received from the pressure regulator at a selected flow rate,
an oxygen distribution assembly including a pneumatic demand oxygen valve and a conduit conducting oxygen discharged from the flow controller to the pneumatic demand oxygen valve for delivery to a patient, the pressure regulator being positioned to lie between the flow controller and the pneumatic demand oxygen valve,
first detachable connector means for detachably connecting the flow controller to the pressure regulator, and
second detachable connector means for detachably connecting the pneumatic demand oxygen valve to the pressure regulator.

25. The apparatus of claim 24, wherein the pressure regulator includes a modular regulator body, the flow controller includes a modular flow controller housing, the pneumatic demand oxygen valve includes a modular valve body, the first detachable connector means includes at least one fastener coupling the modular flow controller housing to one side of the modular regulator body, and the second detachable connector means includes at least one fastener coupling the modular flow controller housing to another side of the modular regulator body.

26. The apparatus of claim 25, wherein the modular flow controller housing includes a mounting orientation post, the modular valve body includes a mounting orientation post, the one side of the modular regulator body is formed to include an aperture receiving the mounting orientation post of the modular flow controller housing, and the another side of the modular regulator body is formed to include an aperture receiving the mounting orientation post of the modular valve body.

27. The apparatus of claim 25, wherein the one side of the modular regulator body faces in a first direction and the another side of the modular regulator body faces in a second direction opposite to the first direction.

28. Apparatus for controlling discharge of oxygen from an oxygen supply source to a patient, the apparatus comprising
an oxygen supply inlet,
a modular pressure regulator coupled to the oxygen supply inlet and configured to reduce pressure of oxygen received from the oxygen supply inlet to a selected magnitude,
a modular flow controller configured to meter oxygen received from the pressure regulator at a selected flow rate,
a first connector coupled to the modular pressure regulator and to the modular flow controller to position the modular pressure regulator adjacent to the modular flow controller and to communicate oxygen from the modular pressure regulator to the modular flow controller,
an oxygen distribution assembly including a modular pneumatic demand oxygen valve and a conduit conducting oxygen discharged from the modular flow controller to the modular pneumatic demand oxygen valve for delivery to a patient, and
a second connector coupled to the modular pressure regulator and the modular pneumatic demand oxygen valve to position the modular pneumatic demand oxygen valve adjacent to the modular pressure regulator.

29. The apparatus of claim 28, wherein the modular flow controller includes a mounting orientation post, the modular pneumatic demand valve includes a mounting orientation post, and the modular pressure regulator is formed to include a first aperture receiving the mounting orientation post of the modular flow controller and a second aperture receiving the mounting orientation post of the modular pneumatic demand valve.

30. The apparatus of claim 29, wherein the modular pressure regulator includes a first side wall formed to include the first aperture and a second side wall formed to include the second aperture.

31. The apparatus of claim 30, wherein the first side wall faces in a first direction and the second side wall faces in a second direction opposite to the first direction.

32. The apparatus of claim 29, wherein the mounting orientation post of the modular flow controller is positioned to lie in spaced-apart relation to the first connector and the mounting orientation post is configured to lie in spaced-apart relation to the second connector.

33. The apparatus of claim 28, wherein the modular pressure regulator and the modular flow controller are positioned to lie in side-by-side relation.

34. The apparatus of claim 32, wherein the modular pressure regulator abuts the modular flow controller.

35. The apparatus of claim 28, wherein the modular pressure regulator and the modular pneumatic demand oxygen valve are positioned to lie in side-by-side relation.

36. The apparatus of claim 35, wherein the modular pressure regulator abuts the modular flow controller.

37. The apparatus of claim 28, wherein the conduit includes an inlet end coupled to the modular flow controller, an outlet end coupled to the modular pneumatic demand oxygen valve, and a middle portion interconnecting the inlet and outlet ends and passing through the modular pressure regulator.

38. The apparatus of claim 37, wherein the oxygen distribution assembly further includes an auxiliary conduit conducting oxygen from the modular flow controller to a valve member mounted in a space formed in the modular pneumatic demand valve in communication with the conduit to control oxygen flow from the conduit to a patient through the modular pneumatic demand valve, the modular pressure regulator is formed to include a portion of the pressure regulator.

39. The apparatus of claim 28, wherein the oxygen distribution assembly further includes an auxiliary conduit conducting oxygen from the modular flow controller to a valve member mounted in a space formed in the modular pneumatic demand valve in communication with the conduit to control oxygen flow from the conduit to a patient through the modular pneumatic demand valve, the modular pressure regulator is formed to include a portion of the pressure regulator.

40. The apparatus of claim 28, wherein the modular pneumatic demand valve includes a diaphragm valve member communicating with the conduit and an inhale/exhale sensing diaphragm pneumatically coupled to the diaphragm valve member and the modular flow controller includes an internal chamber and means for splitting the flow of oxygen received in the internal chamber from the modular pressure regulator into a first oxygen stream discharged into the conduit and a second oxygen stream, and the apparatus further comprises means for selectively communicating the second oxygen stream to the diaphragm valve member in the modular pneumatic demand valve.

41. An apparatus for controlling discharge of oxygen from an oxygen supply source to a patient through a breathing line coupled to the patient as the patient inhales and exhales, the apparatus comprising an oxygen supply inlet, a modular pressure regulator coupled to the oxygen supply inlet and configured to reduce pressure of oxygen received from the oxygen supply inlet to a selected magnitude, a modular flow controller configured to meter oxygen received from the pressure regulator at a selected flow rate, means for conducting oxygen provided by the modular flow controller through a supply passageway having a gas inlet coupled to the modular flow controller and a gas outlet for attachment to a breathing line, the conducting means including a valve seat in the supply passageway, means for storing a supply of oxygen extant in the supply passageway in a first chamber to develop a pressure head in the first chamber, the storing means including auxiliary conduit means for admitting oxygen from the modular flow controller into the first chamber and outlet means for discharging oxygen from the first chamber to the atmosphere, means for selectively blocking flow of oxygen through the supply passageway from the gas inlet to the gas outlet, the blocking means including a flexible diaphragm valve member including a first side communicating with oxygen admitted into the first chamber and a second side facing the valve seat in the supply passageway, the diaphragm valve member being mounted for movement between a flow-blocking position engaging the valve seat in the supply passageway and a flow-delivery position disengaging the valve seat in the supply passageway, and control means for closing the outlet means during exhalation of a patient breathing thorough the gas outlet to store pressurized oxygen in the first chamber so that oxygen pressure in the first chamber acting against the first side of the diaphragm valve member will increase to move the diaphragm valve member to its flow-blocking position and opening the outlet means in response to inhalation of a patient breathing through the gas outlet to vent pressurized oxygen in the first chamber to the atmosphere through the outlet means so that oxygen pressure in the first chamber will decrease to allow pressurized oxygen in the supply passageway to move the diaphragm valve member away from the valve seat to its flow-delivery position, the modular flow controller including an internal chamber and means for selectively splitting the flow of oxygen received in the internal chamber from the modular pressure regulator into a first oxygen stream discharged into the supply passageway for distribution to a patient and a second oxygen stream discharged into the auxiliary conduit means for distribution to the first chamber.

42. Apparatus for controlling discharge of oxygen from an oxygen supply source to a patient, the apparatus comprising a flow controller housing formed to include a sealed internal chamber having an oxygen-receiving inlet adapted to be coupled to an oxygen supply source, a first oxygen-discharging outlet, and a second oxygen-discharging outlet, and a flow control valve positioned in the sealed internal chamber for movement relative to the flow controller housing between a first position range discharging oxygen from the sealed internal chamber through the first oxygen-discharging outlet and through the second oxygen-discharging outlet and a second position range discharging oxygen from the sealed internal chamber through the first oxygen-discharging outlet without discharging oxygen from the sealed internal chamber through the second oxygen-discharging outlet.

43. The apparatus of claim 42, wherein the flow control valve is also positioned in the sealed internal chamber for movement relative to the flow controller housing to a third position range blocking flow of oxygen from the sealed internal chamber through the first and second oxygen-discharging outlets.

44. The apparatus of claim 43, wherein the flow control valve includes a rotor disk positioned in the sealed internal chamber to receive oxygen admitted into the sealed internal chamber through the oxygen-receiving inlet and a shaft mounted in the housing to support the rotor disk for rotational movement in the sealed internal chamber about an axis of rotation between the first, second and third position ranges.

45. The apparatus of claim 44, wherein the rotor disk is formed to include a plurality of oxygen flow-metering apertures conducting oxygen from the sealed internal chamber to the first oxygen-discharging outlet upon movement of the flow control valve to the first position range and a flow-shut off plate positioned to lie between two of the oxygen flow-metering apertures and to block flow of oxygen from the sealed internal chamber into the first oxygen-discharging outlet upon movement of the rotor disk in the sealed internal chamber to the third position range.

46. The apparatus of claim 45, wherein the rotor disk is formed to include a C-shaped oxygen flow channel having opposite ends and a flat wall portion extending between the opposite ends of the C-shaped oxygen flow channel, the C-shaped oxygen flow channel is positioned to communicate oxygen therethrough from the sealed internal chamber to the second oxygen-discharging outlet upon movement of the flow control valve to the first position range, and the flat wall portion is positioned to block flow of oxygen from the sealed internal chamber to the second oxygen-discharging outlet upon movement of the flow control valve to one of the second and third position ranges.

47. The apparatus of claim 46, wherein the rotor disk includes a front face and an opposite rear face, the front face is formed to include the flow-shut off plate, the C-shaped oxygen flow channel, the flat wall portion, and an outlet of each of oxygen flow-metering aperture, and the rear face is formed to include an inlet of each oxygen flow-metering aperture.

48. The apparatus of claim 42, wherein the flow control valve includes a rotor disk positioned in the sealed internal chamber to receive oxygen admitted into the sealed internal chamber through the oxygen-receiving inlet and a shaft mounted in the housing to support the rotor disk for rotational movement in the sealed internal chamber about an axis of rotation between the first and second position ranges.

49. The apparatus of claim 48, wherein the rotor disk is formed to include a plurality of oxygen flow-metering apertures, each of the oxygen flow-metering apertures includes a flow restriction passage of a predetermined internal diameter, and each of the oxygen flow-metering apertures is located in the rotor disk to conduct oxygen from the sealed internal chamber to the first oxygen-discharging outlet upon rotation of the rotor disk about the axis of rotation to move the flow control valve to one of the first and second position ranges.

50. The apparatus of claim 49, wherein the rotor disk is formed to include a rear face facing in a first direction toward the shaft and a front face facing in a second direction opposite to the first direction, the rear face is formed to include an inlet opening for each oxygen flow-metering aperture receiving oxygen extant in the sealed internal chamber, and the front face is formed to include an outlet opening for each oxygen flow-metering aperture discharging oxygen into the first oxygen-discharging outlet upon movement of the flow control valve to one of the first and second position ranges.

51. The apparatus of claim 50, wherein the front face is also formed to include a C-shaped oxygen flow channel having opposite ends and a flat wall portion extending between the opposite ends of the C-shaped oxygen flow channel, the C-shaped oxygen flow channel is positioned to communicate oxygen therethrough from the sealed internal chamber to the second oxygen-discharging outlet upon movement of the flow control valve to the first position range, and the flat wall portion is positioned to block flow of oxygen from the sealed internal chamber to the second oxygen-discharging outlet upon movement of the flow control valve to the second position range.

52. A flow controller for use in an apparatus for controlling discharge of oxygen from an oxygen supply source to a patient, the flow controller comprising a modular housing formed to include a sealed internal chamber, an inlet conduit adapted to be coupled to an oxygen supply source and configured to conduct oxygen from the oxygen supply source into the sealed internal chamber, a first outlet positioned to conduct a first stream of oxygen discharged from the sealed internal chamber toward a first point of use, and a second outlet positioned to conduct a second stream of oxygen discharged from the sealed internal chamber toward a second point of use, a valve positioned to lie in the sealed internal chamber formed in the modular housing for movement from a first position range placing the inlet conduit in fluid communication with both of the first and second outlets so that oxygen flowing into the sealed internal chamber is split to cause the first stream to flow out of the sealed internal chamber through the first outlet and the second stream to flow out of the sealed internal chamber through the second outlet to a second position range placing the inlet conduit in fluid communication only with the first outlet so that oxygen flowing into the sealed internal chamber is discharged through the first outlet without flowing through the second outlet, and a valve controller coupled to the modular housing to move the valve in the sealed internal chamber between the first and second position ranges.

53. The flow controller of claim 52, wherein the valve controller includes a shaft coupled to the modular housing for rotation about an axis and the shaft includes an inner end coupled to the valve to support the valve for rotation about the axis during movement of the valve between the first position range and the second position range.

54. The flow controller of claim 53, wherein the shaft includes an outer end and the flow controller further includes a flow selector knob coupled to the outer end of the shaft and configured to be gripped by a user to rotate the shaft and the valve about the axis to position the valve in one of the first and second position ranges.

55. The flow controller of claim 54, wherein the modular housing includes a mounting plate and an interface plate coupled to the mounting plate to define the sealed internal chamber therebetween, the interface plate is positioned to lie between the mounting plate and the flow selector knob and is configured to support the shaft for rotation about the axis, and the mounting plate is formed to include the inlet conduit and the first and second outlets.

56. The flow controller of claim 54, further comprising a detent mechanism mounted in the modular housing in spaced-apart relation to the shaft to fix the position of the rotatable valve in one of several predetermined fixed positions within the modular housing to retain the valve in a selected one of the first and second position ranges.

57. The flow controller of claim 53, wherein the valve includes a rear face coupled to the shaft and a front face arranged to face away from the shaft, the valve is formed to include a plurality of oxygen flow-metering apertures situated to lie in fluid communication with the inlet conduit and the first outlet when the valve lies in the first and second position ranges, and each flow-metering aperture is defined by an inlet formed in the rear face, an outlet formed in the front face, and a flow-restriction passage interconnecting an inlet and a companion outlet.

58. The flow controller of claim 57, wherein the front face of the valve is formed to include a C-shaped oxygen flow channel having opposite ends and a flat wall portion extending between the opposite ends of the C-shaped flow channel, the C-shaped flow channel is positioned to communicate oxygen therethrough from the sealed internal chamber to the second outlet upon movement of the valve to the first position range, and the flat wall portion is positioned to block flow of oxygen from the sealed internal chamber to the second outlet upon movement of the valve to the second position range.

59. The flow controller of claim 53, wherein the valve includes a rear face coupled to the shaft and a front face arranged to face away from the shaft and the valve is formed to include a plurality of oxygen flow-metering apertures having openings in the front and rear faces and a C-shaped oxygen flow channel formed in the front face to communicate oxygen therethrough from the sealed internal chamber to the second outlet only upon movement of the valve to the first position range.

60. The flow controller of claim 59, wherein the front face of the valve is formed to include a ring of openings into the oxygen flow-metering apertures surrounding the C-shaped oxygen flow channel.

61. The flow controller of claim 59, further comprising a detent mechanism mounted in the modular housing in spaced-apart relation to the shaft to fix the position of the rotatable valve in one of several predetermined fixed positions within the modular housing to retain the valve in a selected one of the first and second position ranges, the rear face of the valve is formed to include an outer ring of openings into the oxygen flow-metering apertures, and the rear face of the valve is also formed to include an inner ring of circumferentially spaced-apart depressions configured to receive the detent mechanism therein.

62. The flow controller of claim 52, wherein the modular housing includes a mounting plate formed to include the inlet conduit and the first and second outlets, a first O-ring seal stack mounted in the first outlet to support and sealingly engage the valve, and a second O-ring seal stack mounted in the second outlet to support and sealingly engage the valve.

63. The flow controller of claim 62, wherein the valve includes a rear face coupled to the valve controller and a front face sealingly engaging the first and second O-ring stacks during movement of the valve in the sealed internal chamber and when the valve is stationary.

64. The flow controller of claim 63, wherein the valve controller includes a shaft coupled to the modular housing for rotation about an axis and the shaft includes an inner end coupled to the rear face to support the valve for rotation about the axis and sealing engagement with the first and second O-ring seal stacks.

65. The flow controller of claim 63, wherein the valve is formed to include a plurality of oxygen flow-metering apertures having openings in the front and rear faces and being positioned to communicate oxygen therethrough from the sealed interior chamber through an oxygen-conducting passage defined by the first O-ring seal stack in the first outlet when the valve lies in the first and second position ranges and a C-shaped oxygen flow channel formed in the front face to communicate oxygen therethrough from the sealed interior chamber through an oxygen-conducting passage defined by the second O-ring seal stack in the second outlet only upon movement of the valve to the first position range.

* * * * *